(12) United States Patent
Richardson et al.

(10) Patent No.: US 11,083,855 B2
(45) Date of Patent: Aug. 10, 2021

(54) AUTO-RESET DOSE RELEASE FIRING SYSTEMS, MEDICINAL INHALERS COMPRISING SAME, AND METHODS OF USING SAME

(71) Applicant: KINDEVA DRUG DELIVERY L.P., St. Paul, MN (US)

(72) Inventors: William T. Richardson, Royston (GB); John P. Bunting, Castle Donington (GB); Peter D. Hodson, Breaston (GB); Christopher B. J. Groombridge, Stevenage (GB); David J. Cottenden, Melbourn (GB)

(73) Assignee: Kindeva Drug Delivery L.P., St. Paul, MN (US)

( * ) Notice: Subject to any disclaimer, the term of this patent is extended or adjusted under 35 U.S.C. 154(b) by 377 days.

(21) Appl. No.: 16/064,413

(22) PCT Filed: Dec. 13, 2016

(86) PCT No.: PCT/US2016/066292
§ 371 (c)(1),
(2) Date: Jun. 20, 2018

(87) PCT Pub. No.: WO2017/112451
PCT Pub. Date: Jun. 29, 2017

(65) Prior Publication Data
US 2019/0022339 A1    Jan. 24, 2019

Related U.S. Application Data

(60) Provisional application No. 62/270,070, filed on Dec. 21, 2015.

(51) Int. Cl.
| | |
|---|---|
| *A61M 15/00* | (2006.01) |
| *B65D 83/38* | (2006.01) |
| *B65D 83/16* | (2006.01) |

(52) U.S. Cl.
CPC ...... *A61M 15/009* (2013.01); *A61M 15/0091* (2013.01); *B65D 83/16* (2013.01); *B65D 83/386* (2013.01); *A61M 15/002* (2014.02)

(58) Field of Classification Search
CPC ............ A61M 15/0091; A61M 15/009; A61M 15/002; A61M 15/0093; A61M 2205/276;
(Continued)

(56) References Cited

U.S. PATENT DOCUMENTS

| | | |
|---|---|---|
| 4,414,972 A | 11/1983 | Young et al. |
| 5,217,004 A | 6/1993 | Blasnik et al. |

(Continued)

FOREIGN PATENT DOCUMENTS

| | | |
|---|---|---|
| EP | 0 147 028 | 7/1985 |
| EP | 0 490 797 | 6/1992 |

(Continued)

*Primary Examiner* — Victoria Murphy
(74) *Attorney, Agent, or Firm* — Mueting Raasch Group

(57) ABSTRACT

An auto-reset dose release firing system (101) and a method of using same. The system can include an a stored energy device (109); a first plunger (103) movable between first, second, and third positions, the first plunger configured to be operatively coupled to a medicament canister (51); and a second plunger (104) movable between first and second positions; the first and second plunger being movable with respect to one another and shaped to define an evacuable chamber (185) therebetween. The first plunger and the second plunger can move together from their respective first positions to their respective second positions, due to a reduced pressure in the chamber, to cause a dose release valve (54) to fire. After firing, air can be allowed to move into the chamber to allow the first plunger to move with respect to the second plunger to its third position to allow the dose release valve to reset.

16 Claims, 20 Drawing Sheets

(58) Field of Classification Search
CPC ....... B65D 83/386; B65D 83/16; A24F 42/20; B05B 11/309; B05B 11/3091
See application file for complete search history.

(56) References Cited

U.S. PATENT DOCUMENTS

| | | |
|---|---|---|
| 5,347,998 A | 9/1994 | Hodson et al. |
| 5,450,336 A | 9/1995 | Rubsamen et al. |
| 5,954,047 A | 9/1999 | Armer et al. |
| 6,240,918 B1 | 6/2001 | Ambrosio et al. |
| 6,328,035 B1 | 12/2001 | Wakefield et al. |
| 6,581,590 B1 | 6/2003 | Genova et al. |
| 6,637,432 B2 | 10/2003 | Wakefield et al. |
| 6,668,826 B1 | 12/2003 | Myrman |
| 7,299,800 B2 | 11/2007 | Stradella |
| 7,363,924 B2 | 4/2008 | Stradella |
| 8,286,837 B1 | 10/2012 | Blake |
| 2002/0000225 A1 | 1/2002 | Schuler et al. |
| 2002/0189612 A1 | 12/2002 | Rand |
| 2003/0005926 A1 | 1/2003 | Jones et al. |
| 2003/0079744 A1 | 5/2003 | Bonney et al. |
| 2004/0050385 A1 | 3/2004 | Bonney et al. |
| 2005/0022806 A1 | 2/2005 | Beaumont et al. |
| 2006/0137681 A1 | 6/2006 | Von Hollen et al. |
| 2006/0231093 A1 | 10/2006 | Burge et al. |
| 2008/0178872 A1 | 7/2008 | Genova et al. |
| 2012/0010575 A1 | 1/2012 | Jones et al. |
| 2012/0103329 A1 | 5/2012 | Smith |

FOREIGN PATENT DOCUMENTS

| | | | |
|---|---|---|---|
| GB | 2 266 466 | 11/1993 | |
| GB | 2 398 254 | 8/2004 | |
| GB | 2398254 A * | 8/2004 | ........ A61M 15/0083 |
| KR | 10-2015-0118195 | 10/2015 | |
| WO | WO 1992/07600 | 5/1992 | |
| WO | WO 1992/09323 | 6/1992 | |
| WO | WO 1992/12799 | 8/1992 | |
| WO | WO 2001/41845 | 6/2001 | |
| WO | WO 2001/41847 | 6/2001 | |
| WO | WO 2001/41849 | 6/2001 | |
| WO | WO 2002/100469 | 12/2002 | |
| WO | WO 2006/106367 | 10/2006 | |
| WO | WO 2008/070516 | 6/2008 | |
| WO | WO 2015/034709 | 3/2015 | |
| WO | WO 2017/112400 | 6/2017 | |
| WO | WO 2017/112452 | 6/2017 | |
| WO | WO 2017/112476 | 6/2017 | |
| WO | WO 2017/112748 | 6/2017 | |

\* cited by examiner

AUTO-RESET DOSE RELEASE FIRING SYSTEMS, MEDICINAL INHALERS COMPRISING SAME, AND METHODS OF USING SAME

CROSS REFERENCE TO RELATED APPLICATIONS

This application is a national stage filing under 35 U.S.C. 371 of PCT/US2016/066292, filed Dec. 13, 2016, which claims the benefit of U.S. Provisional Patent Application No. 62/270,070, filed Dec. 21, 2015, the disclosure of which is incorporated by reference in its entirety herein.

FIELD

The present disclosure generally relates to an auto-reset dose release firing system for use in medicinal inhalers, and medicinal inhalers comprising the auto-reset dose release firing system.

BACKGROUND

Delivery of aerosolized medicament to the respiratory tract for the treatment of respiratory and other diseases is conventionally done using inhalers of either the pressurised metered dose inhaler (pMDI), the dry powder inhaler (DPI) or the nebulizer type. pMDI inhalers in particular have become an industry standard, and are familiar to many patients who suffer from either asthma or from chronic obstructive pulmonary disease (COPD). Conventional pMDI devices comprise an aluminum canister, sealed with a metering valve, which contains the medicament formulation. Generally, the medicament formulation is a pressurized formulation containing either fine particles of one or more medicinal compounds suspended in a liquefied hydrofluoroalkane (HFA) propellant, or a solution of one or more medicinal compounds dissolved in a propellant/co-solvent system. Formulations incorporating one drug in solution and another one in suspension form are also known.

In a conventional pulmonary pMDI, the sealed canister is provided to the patient in an actuator. The actuator is conventionally a generally L-shaped plastic molding comprising a generally cylindrical vertical tube that surrounds the canister plus a generally horizontal tube that forms a patient portion (e.g., a mouthpiece or nosepiece) that defines an inspiration (or inhalation) orifice. To use such an inhaler, the patient exhales, places the patient port into a body cavity (e.g., a mouth or nose) and then inhales to draw air through the inspiration orifice. The majority of such inhalers are of the pulmonary "press-and-breathe" type, where the patient must press down on the protruding end of the canister in order to operate the metering valve to release a metered dose of medicament from the canister into the inhaled air stream and thence through the mouthpiece into their lungs. This requires a significant degree of coordination of timing of inhalation and dose release if the emerging cloud of aerosolized medicament is to be taken far enough into the lungs to provide maximum therapeutic benefit. If the patient releases the dose before inspiratory flow has been established, then a proportion of the drug is likely to be lost in the mouthpiece or the patient's mouth. Conversely, if released much after the start of inhalation, then the deeper regions of the lungs might already be full of air and not penetrated by the following bolus of released medicament aerosol.

Spacer devices have previously been devised which fit onto the mouthpiece of a pMDI in order to reduce the velocity of the emergent plume of medicament aerosol and to provide a volume in which it can expand and its propellant can evaporate more completely. This serves to avoid some of the problems of coordination and also avoids the tendency for high throat deposition caused by excessively fast drug particle inhalation. However, spacer devices are very bulky, and they can retain an excessive proportion of the drug on their walls, thereby reducing the dose that reaches the patient. Spacer devices can also be highly sensitive to electrostatic charge, which can often be strongly affected by the way in which they are washed or dried.

To overcome what can be quite a challenge for some patients, pMDI device designs have been created that employ automatic breath-actuated triggering, releasing a dose only in response to the patient's inhaled breath. The AUTOHALER™ metered dose inhaler, available from 3M Company, St. Paul, Minn., and the EASIBREATHE™ inhaler, available from Teva Pharmaceutical Industries Ltd., Israel, are two such pMDI devices that use breath-actuation to attempt to better coordinate dose release with inhalation.

US20050022806 A1 discloses medicament dispensers. One embodiment shows a wire-assisting means comprising a rotatable cylinder comprising a downwardly spiralling guide track and a clutch at the centre thereof. A number of coupling wires are radially attached to the top of the cylinder, the other end of the coupling wires being attached to a fixed point of the dispenser (not shown). A guide arm is connected to a cap, the cap fitting over a medicament container which sits in a collar. Located between the bottom of the cylinder and the top of the cap is a spring. The guide arm is locatable within the guide track. As the device is activated, the coupling wires contract, causing cylinder to rotate. As it rotates, the spiralling guide track causes the guide arm to move downwards in a vertical manner, the cap causing the medicament container to move to a dispensing position.

US2002189612 A1 and US2003005926 A1 disclose medicament dispensers. As the patient inhales, a breath sensor (not shown) registers the patient's breath, completes an electrical circuit (not shown), the current from which heats a trigger coupling or in this case, a firing shape memory alloy (SMA) wire which is linked to the firing cam lock. As the SMA wire increases in temperature it contracts, and in doing so removes the firing cam lock from the firing lever. The tension spring now releases its energy and recoils upwards and pivots the firing lever downwards thus pulling the canister down relative to the valve to release a dose of medicament through the mouthpiece of the inhaler.

U.S. Pat. No. 6,637,432 discloses a device for dispensing medication in an aerosol from an MDI which is activated by a source of compressed air which is pressurized by a compression piston in association with a cocking lever which also acts as a mouthpiece cover wherein the device automatically discharges the medication upon inhalation on the mouthpiece. A bleed orifice in the crown of the actuation piston slowly bleeds off the compressed air contained between the upper surface and the piston, permitting the canister return spring to push the piston back to its original position, without user intervention. The dwell time and air bleeding function of the bleed orifice is implemented by using a porous (7 μm) membrane inserted into a bore of the actuation piston where the bleed orifice is located. Using a porous membrane minimizes the chance that the bleed orifice becomes blocked or obstructed by debris.

U.S. Pat. No. 6,637,432 discloses an inhalation actuated dispensing apparatus where movement of the cover relative to the housing spring loads and latches a piston carrier in the armed position. Inhalation causes a passageway door to open, releasing the carrier latch to permit the carrier to be moved toward the canister by a spring. The piston moves with the carrier, due to a fluid connection therebetween, applying a compression force on the spring loaded canister valve stem and causing it to dispense the inhalant through an opening in the piston which functions as a nozzle. After the inhalant is dispensed, the carrier fluid vents permitting the spring of the canister valve stem to move the piston relative to the carrier, and thus release the force applied to the valve stem by the piston.

SUMMARY

Even though breath-actuated inhalers can be a useful aid in achieving coordination between inhalation and medicament dose release, some of the existing devices employ mechanical breath-actuation systems that typically need to be tightly toleranced in order to be both stable and yet also sensitive. The nature of stored energy mechanical breath-actuation systems is such that typically a large load of several tens of Newtons (e.g., held in a compression spring) needs to be held back (i.e., prevented from release) by a latching mechanism that has to be unlatched using only the force of the patient's breath (e.g., 1 Newton, from a reasonably sized vane). That requires a large 'mechanical advantage', whereby a small force can release a much larger one. For example, typical pMDI metering valves can require over 40 N to fire them, meaning that a compression spring to drive them needs to provide in excess of that force even after it has moved the valve by around 2-3 mm or so: i.e., it needs to provide >40 N even at the point where it has already unloaded by 2-3 mm from its compressed state at which the firing mechanism was primed (or 'cocked'). Fully mechanical systems providing such a degree of 'mechanical advantage' are typically both complex and finely tuned, which can include needing to have carefully controlled dimensions.

In some embodiments of the present disclosure, firing systems can be employed in combination with an electronically-triggered breath-actuation system, which can function to release (or unlatch) the firing system, allowing it to change to its fired state. In such embodiments, the addition of electronics to an inhaler can allow other functionality to be "piggy-backed" onto the triggering system electronics. For example, an electronic dose counter can be added, as can electronic timing, generation of usage reminders, etc. If electronic pressure sensors are used to detect the presence of air flow, the magnitude and potentially also the direction of inspiratory air flow through the inhaler, with logic circuit algorithms used to actuate the firing system, then there is also the possibility of recording the inspiratory flow profiles of patients, e.g. for storage and/or analysis as a means of providing the patient and/or their physician with information or advice.

The present inventors further recognized that with any breath-actuated inhaler, the events after the dose has been delivered (e.g., via the pMDI metering valve) can also be important. For example, a problem that can exist with some systems is that the pMDI metering valve can remain after firing (i.e., after dose release) in its depressed (i.e., fired; valve stem in) state, due to a mechanical load from the breath-actuated firing system continuing to exert its force onto the pMDI canister. To overcome this can require intervention by the patient, e.g., to lower a lever to unload the force from the pMDI's metering valve. If this operation is not performed within a relatively short period of time after dispensing a dose, complications can arise, as the metering chamber of the pMDI metering valve can become vulnerable to intrusion of air. Ingress of air can result in vapor lock of the metering chamber, where the presence of the air can prevent complete filling of the metering chamber with the appropriate volume of medicament for the next dose when the valve is eventually returned to its rest position. Subsequently, the next dose that the user receives can contain a lower than intended quantity of drug due to the incomplete filling of the metering chamber.

A further problem that can be associated with breath-actuated inhaler devices in which inattentive patients can fail to reset the firing mechanism is that formulations of suspended drug particles can start to sediment, cream and/or flocculate during prolonged periods without shaking. As most pMDI metering valves "sample" (i.e., fill with the next dose) at the time of valve stem reset/release, then prolonged delays in releasing the depressed valve stem (e.g., because a patient has forgotten to reset a breath-actuated inhaler's firing mechanism after use) can result in inhomogeneous sampling of the next dose from the remaining bulk formulation in the pMDI canister.

For example, a creaming formulation may be under-sampled (i.e., an inappropriately low amount of drug may be present in the liquid of the next dose) if too long a delay occurs between shaking of the inhaler (e.g., pMDI) and the time at which the valve stem is allowed to reset. As a result, drug particles may have preferentially creamed (i.e., risen) away from the vicinity of the sampling port(s) of the valve. Conversely, a sedimenting formulation may tend to be over-sampled if its suspended drug loading is given excessive time to settle into the vicinity of the valve. Flocculating formulations may show additional undesirable effects, e.g., the "floccs" of associated suspended particles may become too large to pass readily into the metering valve, effectively being partially filtered out by its sampling port(s), leading to a potentially low next dose.

In addition, the admission into the metering chamber of ambient air containing moisture, e.g., by diffusion, can create problems of medicament formulation stability, etc.

Therefore it can be desirable to include a mechanism in an inhaler that allows the valve (e.g., in a pMDI) to automatically return to its rest or reset position. However it is also of importance that such a mechanism allows the entire dose to exit the valve, to ensure that the patient receives the intended dose, e.g., that the mechanism does not allow the automatic return of the metering valve to its rest position until full dose release has taken place. For a typical pMDI metering valve, a dose delivery time of 0.5 seconds is generally sufficient for full dose release. Accordingly, it can be desirable to provide a means to ensure a delay time of at least 0.5 seconds between valve actuation (e.g., stem depression in a pMDI canister valve) and valve reset (e.g., stem release in a pMDI canister valve). For a typical pMDI suspension formulation, it can be desirable that only a few seconds pass between the time of shaking and the time of valve reset (i.e., the time of sampling of the next dose). Accordingly, it can also be desirable to provide a means to ensure a delay time of no more than 5-10 seconds between valve actuation (e.g., stem depression) and valve reset (e.g., stem release).

In order to overcome some of the above-described issues relating to inhaler "firing" mechanisms, and particularly, breath-actuated firing mechanisms, and the desirability of incorporating a metering valve auto-release/reset function operated automatically after an appropriate time delay, the present inventors developed the auto-reset dose release firing systems of the present disclosure. These systems can provide reliable operation of an inhaler (and, e.g., a pMDI canister) to dispense a predetermined dose of medicament (e.g., in some embodiments, a metered dose of medicament in response to an electrical signal created when a patient's inspiratory breath is detected through the inhaler), with the valve actuation being automatically released to reset itself after an appropriate time delay of, e.g., 0.5-10 seconds.

Some aspects of the present disclosure provide an auto-reset dose release firing system for use in a medicinal inhaler. The system can include an axis that defines an axial direction that extends along or substantially parallel to the axis; and a stored energy device. The firing system is in a primed state when stored energy of the stored energy device is not released, and the firing system is in a fired state when the stored energy is released. The system can further include a first plunger movable in the axial direction between a first position, a second position, and a third position, wherein the first plunger is configured to be operatively coupled to a medicament canister of the medicinal inhaler to actuate a dose release valve of the medicament canister when the first plunger is in the second position. The system can further include a second plunger movable in the axial direction between a first position and a second position, wherein the second plunger is not configured to be coupled to the medicament canister, wherein the second plunger is positioned to be driven by the stored energy device of the firing system from its first position to its second position when the stored energy is released, wherein the first plunger and the second plunger are movable with respect to one another in the axial direction and are shaped to define an evacuable chamber therebetween. The first plunger and the second plunger can be separated by a first axial distance when the firing system is in the primed state and the first plunger and the second plunger are each in the first position, the first axial distance being at least zero. In addition, the first plunger and second plunger can be separated by the first axial distance when the firing system is in the fired state and the first plunger and the second plunger are each in the second position. Furthermore, the first plunger and the second plunger can be separated by a second axial distance when the firing system is in a reset state, the second plunger is in the second position, and the first plunger is in the third position. The second axial distance can be nonzero and greater than the first axial distance.

A method for releasing a dose of medicament from a medicinal inhaler. The method can include (i) providing a stored energy device. The firing system is in a primed state when stored energy of the stored energy device is not released, and the firing system is in a fired state when the stored energy is released. The method can further include (ii) providing a first plunger movable along the axis between a first position, a second position, and a third position, wherein the first plunger is configured to be operatively coupled to a medicament canister of the medicinal inhaler to actuate a dose release valve of the medicament canister when the first plunger is in the second position; and (iii) providing a second plunger movable along the axis between a first position and a second position, wherein the second plunger is not configured to be coupled to the medicament canister, wherein the second plunger is positioned to be driven by the stored energy device of the firing system from its first position to its second position when the stored energy is released, wherein the first plunger and the second plunger are movable with respect to one another in the axial direction and are shaped to define an evacuable chamber therebetween. The method can further include (iv) releasing stored energy from the stored energy device to move the second plunger from the first position to the second position; (v) creating a reduced air pressure in the evacuable chamber in response to moving the second plunger from the first position to the second position; (vi) moving the first plunger from the first position to the second position with the second plunger as a result of the reduced air pressure created in the evacuable chamber; and (vii) moving the first plunger from the second position to the third position in response to air entering the evacuable chamber via a vent.

Other features and aspects of the present disclosure will become apparent by consideration of the detailed description and accompanying drawings.

DETAILED DESCRIPTION

Figure 1:
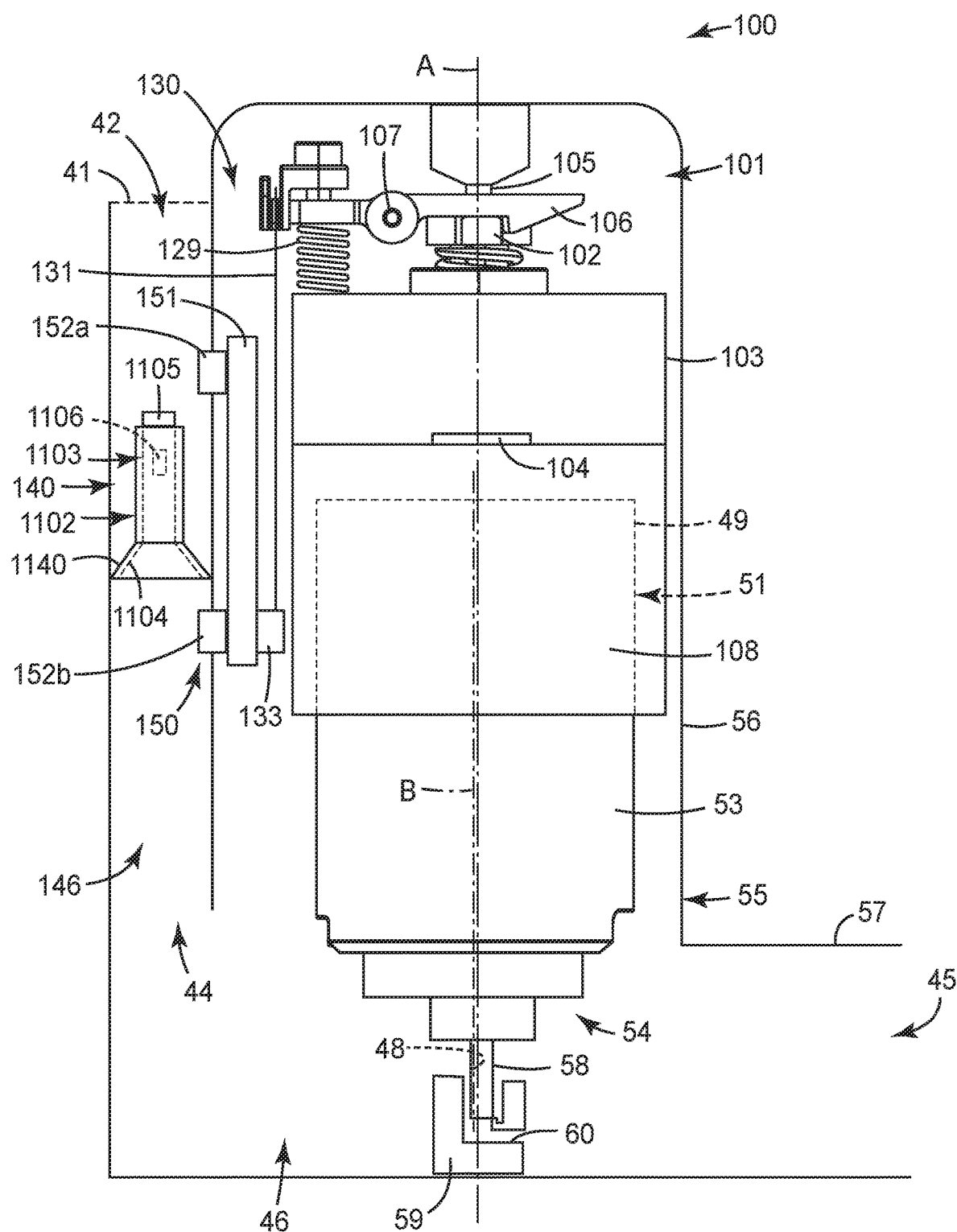
FIG. 1 is a cutaway side elevational view of a medicinal inhaler according to one embodiment of the present disclosure (with a portion of an outer housing removed so that internal components are visible), the inhaler comprising a flow governor according to one embodiment of the present disclosure, an inspiratory air flow detection system according to one embodiment of the present disclosure, and an auto-reset dose release firing system according to one embodiment of the present disclosure, the firing system comprising a trigger according to one embodiment of the present disclosure that includes a shape memory material.

The present disclosure generally relates to auto-reset dose release firing systems for use in medicinal inhalers, and in particular to firing systems suitable for use in various types of inhalers for the delivery of doses of medicament in the form of aerosols to the respiratory tract, including oral pulmonary inhalers and nasal inhalers. In some embodiments, the auto-reset dose release firing systems of the present disclosure can be breath-actuated, responding to a patient's inhalation. For example, in some embodiments, the auto-reset dose release firing system can be electronically breath-actuated, mechanically breath-actuated, or a combination thereof. The firing systems of the present disclosure can also allow a valve (e.g., a metering valve of a pMDI) to automatically reset and refill after an appropriate time delay.

In some embodiments, systems of the present disclosure can provide a valve reset time delay of at least 0.5 seconds; in some embodiments, at least 1 second; and in some embodiments, at least 2 seconds. In some embodiments, valve reset with systems of the present disclosure can be no greater than 10 seconds; in some embodiments, no greater than 9 seconds; in some embodiments, no greater than 8 seconds; in some embodiments, no greater than 7 seconds; in some embodiments, no greater than 6 seconds; and in some embodiments, no greater than 5 seconds. In some embodiments, the time delay can range from 0.5 to 10 seconds, in some embodiments, from 0.5 to 5 seconds, and in some embodiments, from 0.5 to 2 seconds.

Firing systems of the present disclosure can provide the means of releasing a force sufficient to release (i.e., dispense), or fire, a dose of medicament (e.g., a force sufficient to actuate a pMDI valve) with minimal input force. Such systems can be described as providing a mechanical advantage. As described in greater detail below, some embodiments of the present disclosure accomplish this by employing an angled bayonet mechanism to provide the mechanical advantage.

In some embodiments, auto-reset dose release firing systems of the present disclosure can include:
  (i) an axis (e.g., a longitudinal axis) that defines an axial/longitudinal direction that extends along or substantially parallel to the axis;
  (ii) a stored energy device, wherein the firing system is in a primed state when stored energy in the stored energy device is not released, and wherein the firing system is in a fired state when the stored energy is released;
  (iii) a first (e.g., outer, e.g., radially outer) plunger movable in the axial direction (e.g., along the axis) between a first (i.e., starting or primed) axial position, a second (i.e., fired) axial position, and a third (i.e., reset) position (in some embodiments, the third position being the same as the first position), wherein the first plunger is configured to be operatively coupled to a medicament canister of the medicinal inhaler to actuate/open a dose release valve of the medicament canister when the first plunger moves to the second position; and
  (iv) a second (e.g., inner, e.g., radially inner) plunger movable in the axial direction (e.g., along the axis) between a first (i.e., starting or primed) axial position and a second (i.e., fired) axial position, wherein the second plunger is not configured to be coupled to the medicament canister, wherein the second plunger is positioned to be driven by the stored energy device of the firing system from its first position to its second position when the stored energy is released, wherein the first plunger and the second plunger are movable with respect to one another in the axial direction and are shaped to define an evacuable chamber therebetween;
  (v) wherein the first plunger and the second plunger are separated by a first axial distance when the firing system is in the primed state (i.e., stored energy is stored and not released) and the first plunger and the second plunger are each in the first position, wherein the first axial distance is at least zero;
  (vi) wherein the first plunger and second plunger are separated by the first axial distance when the firing system is in the fired state (i.e., stored energy is released) and the first plunger and the second plunger are each in the second position (i.e., such that the canister valve is actuated to be open and a dose is released); and
  (vii) wherein the first plunger and the second plunger are separated by a second axial distance when the firing system is in the fired state (i.e., stored energy is released), the second plunger is in the second position, and the first plunger is in the third position, wherein the second axial distance is nonzero and is greater than the first axial distance.

In some embodiments, auto-reset dose release firing systems of the present disclosure can further include:

(i) a guideway (which can also be referred to as a "recess," a "cam path", or a "camming guide"), wherein at least a portion of the guideway has a helical shape, the guideway having a first (e.g., upper) portion having a first helix angle with respect to the axis that is greater than zero (i.e., the first portion is a helical portion of the guideway), and a second (e.g., lower) portion having a second helix angle with respect to the axis, wherein the second helix angle is less than the first helix angle; and (ii) a projection dimensioned to be received in the guideway, the projection and the guideway being movable with respect to one another between a first position corresponding to the first position of the second plunger and a second position corresponding to the second position of the second plunger, such that the projection is configured to be cammed along the guideway when the stored energy device (i.e., by stored energy being released from the stored energy device) drives the second plunger to move (i.e., in the axial direction) between the first position and the second position (i.e., at least partially as the projection travels in the second portion of the guideway);

(iii) where the guideway or the projection is fixedly coupled to the second plunger. (In some embodiments, the guideway or the projection can be integrally formed with the second plunger.)

The guideway and the projection of such embodiments can together provide a bayonet interaction or mechanism, and particularly, in view of the first portion of the guideway, can provide an angled bayonet mechanism. The guideway can particularly be configured to transfer or convert rotary motion about an axis to more axial (e.g., linear) motion (i.e., in a direction oriented along or parallel to the axis, or at least more along or more parallel to the axis).

In some embodiments, firing systems of the present disclosure can further include a latch movable between:

(i) a first (i.e., latched) position in which the latch is coupled to at least one of the guideway and the projection to inhibit the guideway and the projection from moving relative to one another, the stored energy of the stored energy device is not released, and the firing system is in the primed state, and (ii) a second (i.e., unlatched) position in which the latch is decoupled (i.e., released) from the guideway and the projection, such that the guideway and the projection are free to move relative to one another, the stored energy of the stored energy device is released, and the firing system is free to change to the fired state.

In some embodiments, firing systems of the present disclosure can further include a trigger (or "triggering system," or "actuation mechanism") operatively coupled to the latch and configured to change between a first state and a second state to move the latch between the first position and the second position, respectively (i.e., to allow the firing system to be fired). Various types of triggers can be employed in systems of the present disclosure, as described in greater detail below.

Firing systems of the present disclosure are particularly suitable for use in an electronically triggered, breath-actuated pMDI but could also be incorporated into a dry powder inhaler or nebulizer.

That is, firing systems of the present disclosure are suitable for use in a variety of inhalers, including but not limited to, one or more of a pressurized metered dose inhaler (pMDI) (e.g., a press-and-breathe pMDI, a mechanical (i.e., mechanically triggered) breath-actuated pMDI, an electronic (i.e., an electronically triggered) breath-actuated pMDI, or a combination thereof); a dry powder inhaler (e.g., a single dose (e.g., capsule) DPI, a multi-dose (e.g., tape based, or reservoir based) DPI, or a combination thereof); a nebulizer (e.g., a pocket nebulizer); or a combination thereof.

GB Patent No. 2266466 discloses an exemplary electronically triggered breath-actuated pMDI that could be modified to incorporate a firing system of the present disclosure. PCT Publication No. WO 2015/34709 discloses an exemplary DPI that could be modified to incorporate a firing system of the present disclosure. PCT Publication No. WO 92/12799 discloses an exemplary pocket nebulizer that could be modified to incorporate a firing system of the present disclosure. A firing system of the present disclosure can be used in any of the inhalers disclosed in GB Patent No. 2266466, PCT Publication No. WO 2015/34709, PCT Publication No. WO 92/12799 (each of which is incorporated herein by reference in its entirety), or a combination thereof.

Some embodiments of firing systems of the present disclosure can provide a means of releasing a significant amount of stored energy (e.g., stored in a stored energy device, such as a spring) to operate a pMDI canister aerosol dose dispensing mechanism in response to detection of patient inhalation through a pMDI inhaler.

Firing systems of the present disclosure can avoid the need for bulky spacer devices that are intended to reduce the need for the coordination of inhalation and manual dose actuation. When used in conjunction with data recording of flow rates and other inhaler-use events and data, firing systems of the present disclosure can also improve physician monitoring of chronically ill patients.

Definitions

The terms "a", "an", and "the" are used interchangeably with "at least one" to mean one or more of the elements being described.

The term "and/or" means either or both. For example "A and/or B" means only A, only B, or both A and B.

The terms "including," "comprising," or "having," and variations thereof, are meant to encompass the items listed thereafter and equivalents thereof as well as additional items.

Unless specified or limited otherwise, the terms "connected" and "coupled" and variations thereof are used broadly and encompass both direct and indirect connections and couplings. Further, "connected" and "coupled" are not restricted to physical or mechanical connections or couplings.

The term "flexible" is used to refer to a material and/or structure that collapses or significantly deforms in response to an air pressure differential existing across the material and/or structure in its typical mode of operation. The term 'rigid' is used to refer to a material and/or structure that does not collapse or significantly deform under the forces it experiences in its typical mode of operation. For example, the tubular element of flow governors that can be used in combination with firing systems of the present disclosure is generally flexible and deformable in its normal operation, whereas the internal support structure of such flow governors is generally rigid or non-deformable in its normal operation.

The term "tubular" is used to refer to a hollow structure having one or more walls that define an open passageway therein. In some embodiments, the term "tubular" can more specifically refer to elongated hollow structures. Tubular structures of the present disclosure can have any cross-sectional shape desired (i.e., transverse cross-sectional shape—taken substantially orthogonally with respect to a longitudinal axis of the tubular structure), including, but not limited to, one or more of circular, elliptical or oblong (i.e., having a longer major axis and a shorter minor axis), triangular, rectangular, square, trapezoidal, polygonal, star-shaped, D-shaped, other suitable cross-sectional shapes, or a combination thereof. In some embodiments, tubular structures of the present disclosure can have a circular cross-sectional shape.

The term "non-mechanical energy" generally refers to any energy type that is not mechanical energy, and in some embodiments, can include, but is not limited to, at least one of heat energy, electrical current energy, electrical field energy, magnetic field energy, and a combination thereof.

As used herein, the term "annular" or derivations thereof can refer to a structure having an outer edge and an inner edge, such that the inner edge defines an opening. For example, an annular structure can have a circular or round shape (e.g., a circular ring) or any other suitable shape, including, but not limited to, triangular, rectangular, square, trapezoidal, polygonal, etc., or combinations thereof. Furthermore, an "annulus" of the present invention need not necessarily be symmetrical, but rather can be an asymmetrical or irregular shape; however, certain advantages may be possible with symmetrical and/or circular shapes.

The present disclosure will be described with respect to particular embodiments and with reference to certain drawings, but the invention is not limited thereto. The drawings described are only schematic and are non-limiting. In the drawings, the size of some of the elements may for illustrative purposes be exaggerated and not drawn to scale. Where possible, analogous features in different embodiments have generally been denoted by similar numerals (e.g., 130, 230, 330, etc.).

FIG. 1 illustrates an inhaler 100 according to one embodiment of the present disclosure. The inhaler 100 includes a dose release firing system 101 according to one embodiment of the present disclosure, comprising a trigger (or triggering system) 130 according to one embodiment of the present disclosure. The inhaler 100 is further illustrated by way of example only as including a flow governor 140 according to one embodiment of the present disclosure, and an inspiratory air flow detection system 150 (or "inspiratory flow rate detection system," or "air flow detection system," or "flow rate detection system," or derivations thereof) according to one embodiment of the present disclosure. However, it should be understood that inhalers or the present disclosure need not include a flow governor or inhalation air flow detection system.

FIGS. 2-22 illustrate various details of the auto-reset dose release firing system 101. FIGS. 23-26 illustrate other embodiments of triggers that can be employed with firing systems of the present disclosure.

The overall function and various components of the inhaler 100 of FIG. 1 will now be described before turning to the details of the firing system 101.

As shown in FIG. 1, the inhaler 100 is shown by way of example only as being a pressurized metered dose inhaler (pMDI) comprising a canister 51 containing a medicament formulation, the canister comprising a can 53 sealed with a metering valve 54. The canister 51 sits within a housing (or "actuator") 55 comprising a tubular sleeve portion 56 dimensioned to receive the canister 51, and a portion in the form of an open tubular patient port 57 in the form of a mouthpiece that defines an inspiration orifice (or an air outlet) 45. Such a patient port of an inhaler is sometimes referred to herein as a "mouthpiece" for simplicity. However, it should be understood that such mouthpieces can instead be configured to be nosepieces of nasal inhalers and that the present disclosure can equally apply to nasal inhalers even where not specifically mentioned herein.

A stem portion 58 protrudes from the metering valve 54 and is located and retained by friction in a stem socket 59 formed as an integral part of the housing 55 by way of example only. As shown in FIG. 1, a spray orifice 60 can be formed in the stem socket 59, and can provide a passage for fluid communication between the valve stem portion 58 and the inspiration orifice 45. In use, a patient places the patient port (e.g., mouthpiece) 57 into a body cavity (e.g., mouth) and then inhales through it. However, in the case of nasal pMDIs, it is not always necessary to inhale.

In some embodiments employing a press-and-breathe pMDI, the patient can inhale through the patient port 57 while at the same time pressing downwards on a protruding base of the canister 51. In such embodiments, the pressing force serves to move the canister 51 downwards relative to the valve's stem portion 58. That relative movement between the canister 51 and the valve's stem portion 58 serves to actuate the canister valve 54 to isolate a metered dose of medicament formulation from the bulk formulation in the canister 51 and then to discharge it via a hollow bore 48 formed in the stem portion 58. The discharged dose then passes along the fluid passageway through the stem socket 59 and the spray orifice 60 and emerges in the form of a fine respirable spray that passes through the patient port 57 into the patient's body cavity (e.g., oral cavity and/or nasal cavity) and thence into their respiratory passages, thereby treating their disease.

As the patient inhales on the patient port 57, i.e. as they reduce the air pressure in their own respiratory passages and oral cavity and in the patient port 57 via outward movement of their chest wall and downwards movement of their diaphragm, an air flow is set up through the inhaler 100. Air from the atmosphere external to the inhaler, i.e., ambience, is drawn into the inhaler 100 via an air flow path 46 of the inhaler 100.

In some embodiments, as shown in FIG. 1, employing a breath-actuated pMDI, and particularly, an electronic (or electronically triggered) breath-actuated pMDI, the inhaler 100 can further include the firing system 101 (e.g., the breath-actuated firing system 101) in combination with the inspiratory air flow detection system 150. In such embodiments, the firing system 101 can provide sufficient force to actuate the canister valve 54, i.e., to move the canister 51 downwards relative to the valve's stem portion 58 to release (i.e., dispense) a dose of medicament.

In some embodiments, the inspiratory air flow detection system 150 can include a controller 151 and one or more pressure sensors 152*a*, 152*b* that provide an electrical signal that is used to activate the trigger 130 to trigger the auto-reset dose release firing system 101 to release a dose of medicament according to a defined algorithm. Optionally, the inspiratory air flow detection system 150 and/or the electrical signal generation system may be housed in a reusable module, in order to reduce the overall cost of a prolonged period of treatment.

Generally, the controller 151 can be a suitable electronic device, such as, for example, a programmable logic controller ("PLC"), a programmable circuit board ("PCB"), a microprocessor, and/or other suitable devices or structures. As such, the controller 151 may include both hardware and software components, and the term "controller" is meant to broadly encompass the combination of such components.

In some embodiments, it can be important that the inspiratory flow rate (i.e., volumetric flow rate) at which the firing system 101 triggers is not set too low, to avoid the risk that the breath-actuated inhaler device might operate accidentally or that it will deliver the medicament at too low an inhalation rate for adequate therapeutic effect. It can also be important that the triggering flow rate for the firing system 101 is not set so high that a poorly inhaling patient (e.g., a weak COPD patient) is not able to reach the triggering flow rate.

Furthermore, as shown by way of example only, in some embodiments, the inhaler 100 can further include the flow governor 140 (which can also be referred to as a "flow rate limiter," "flow limiter," "flow regulator," "flow limitation device," or derivations thereof) in combination with the firing system 101. The flow governor 140 can allow appreciable air flow rates at low differential pressures, while increasing air flow resistance at higher differential pressures in order to limit the air flow rates to values more consistent with those obtained at lower differential pressures, in order to reduce inter-patient and intra-patient inhalation variability for the inhaler 100.

In some embodiments, the auto-reset dose release firing system 101 can be controlled by the inspiratory air flow detection system 150, such that the firing system 101 is triggered to release a dose of medicament at a triggering flow rate, i.e., an inspiratory air flow rate, that is less than a governing flow rate of the flow governor 140. That is, the flow governor 140 can be configured to govern air flow rate in the inhaler 100 to a desired air flow rate (i.e., the flow governor 140 can change its geometry in response to the pressure drop it experiences), and the triggering flow rate for the firing system 101 can be set to be lower than the governing flow rate. As a result, when the flow governor 140 and the firing system 101 are used in combination in the same inhaler 100, the firing system 101 can be appropriately triggered at an air flow rate that is not prohibited by the flow governor 140.

Said another way, the triggering flow rate of the firing system 101 needs to be below the governing air flow rate, in order that the latter does not prevent the triggering flow rate from being achieved. For example, in some embodiments, the target triggering flow rate of the inhaler 100 (e.g., of the firing system 101) can be 15 liters/minute (L/min.), and the target governing flow rate can be 30 L/min. Manufacturing tolerances can be maintained such that the inhaler 100 has an actual triggering flow rate of significantly less than its governing flow rate. Environmental factors such as temperature and atmospheric pressure will tend to broaden the range of values actually obtained, but nevertheless actual triggering flow rates might for example vary between 10 L/min. and 20 L/min., and actual governing flow rates might for example vary between 25 L/min. and 35 L/min.

By way of example only, the flow governor 140 is shown as including an outer flexible tubular element (or "tube") 1102 comprising at least one flexible wall 1140, and an internal support structure 1103 that is dimensioned to be received within the tubular element 1102 (i.e., within the at least one flexible wall 1140). In some embodiments, the internal support structure 1103 can include a hollow base 1104, two hollow (e.g., tubular) pillars 1105 (only one of which is visible in FIG. 1) and a cross member 1106 connecting the pillars 1105. Due to the collapsible tubular element 1102 and internal support structure 1103 at least partially positioned within the tubular element 1102, the flow governor 140 is configured to govern air flow by changing its geometry, and thereby its resistance to air flow, as a function of pressure drop between its inlet and its outlet.

Additional details regarding flow governors that can be employed in combination with firing systems of the present disclosure, in inhalers of the present disclosure, can be found in PCT Publication Nos. WO2017/112748, WO2017/112452 and WO2017/112400 each of which is incorporated herein by reference in its entirety. The specific flow governor 140 shown in FIG. 1 is shown by way of example only, and it should be understood that other flow governors can be employed in combination with firing systems of the present disclosure, in inhalers of the present disclosure, without departing from the spirit and scope of the present disclosure.

The flow governor 140 can be positioned in fluid communication with the air flow path 46 of the inhaler 100, and particularly is shown in FIG. 1 by way of example only as being positioned in a dedicated flow governor air flow path 146 positioned in fluid communication with (and thus forming a portion of) the air flow path 46, and thus, in fluid communication with the inspiration orifice 45 of the inhaler 100. Particularly, the inhaler 100 is configured such that inspiratory air necessarily flows through the dedicated air flow path 146 to be governed by the flow governor 140. As shown in FIG. 1, the inhaler 100 can include an air inlet 42, which can define an aspiration orifice, through which air can be drawn into the dedicated air flow path 146, past and/or through the flow governor 140, toward and out of the inspiration orifice 45. In some embodiments, the air inlet 42 can include a grill, screen or grate 41 positioned to inhibit debris from entering the air inlet 42. The dedicated air flow path 146 can further include an air outlet 44 positioned to connect the dedicated air flow path 146 with the rest of the inhaler 100, and particularly, with the inspiration orifice 45.

As shown in FIG. 1, the one or more pressure sensors 152a, 152b can be located in fluid communication with the dedicated air flow path 146. The first pressure sensor 152a can be located upstream of the flow governor 140. The pressure sensors 152a, 152b can be connected to the controller 151, all of which can be powered by a suitable power source with an appropriate switch to provide a power on/off function. When the power is switched on, the pressure sensor 152a can determine the atmospheric pressure. When the patient inhales air through the inhaler 100, causing air to flow out of the air outlet 44, air flows into the air flow path 146 via the air inlet 42, and the pressure sensor 152a detects and/or measures the dynamically changing air pressure brought about by the patient's inspiratory effort in conjunction with the functionality of the flow governor 140.

Detection of pressure changes, relative to the initial atmospheric pressure, via cooperation between the pressure sensor 152a and the controller 151, can be used to calculate the air flow rate past the pressure sensor 152a. (The air flow rate causes a reduction in local air pressure, via the Bernoulli Effect.) When a desired pre-determined flow rate is reached, an electronic signal can be used to enable the firing system 101 to automatically actuate the inhaler 100. Alternatively, the electrical signal can be sent to a suitable component, such as a Light Emitting Diode (LED) or Liquid Crystal Display (LCD) or audio speaker, to provide a cue for the user to actuate the inhaler 100 (e.g., in a mechanically triggered firing system).

Furthermore, in some embodiments, the second pressure sensor 152b can be included in the air flow path 146 towards the air outlet 44 (i.e., downstream of the flow governor 140). The presence of this second pressure sensor 152b can be used to determine air flow direction via comparison of the relative local air pressures at the two pressure sensors 152a, 152b (e.g., performed by the controller 151), which can be used to distinguish inspiration from exhalation (e.g., if a patient blows into the inhaler 100 instead of sucking air through the inhaler 100). This can allow a linked breath-actuation mechanism (e.g., the firing system 101) to be arranged not to operate if the patient breathes out into the inhaler, rather than in through it, the two breathing modes being easily differentiated by the different relative pressure drop relationships detected by the first and second sensors 152a and 152b.

Inclusion of two pressure sensors 152a, 152b in fluid communication with the air flow path 146 enables measurement (in conjunction with the appropriate electrical components, e.g., the controller 151, power source, etc.) of pressure changes, which can be correlated with air flow rates. When a predetermined flow rate is achieved, this can prompt a signal to trigger the firing system 101 to actuate the inhaler canister valve 54. Such a mechanism can negate the requirement for the patient to coordinate inhaling and actuating the inhalation device. In addition, the triggering flow rate can be programmed differently for different products. In each case, though, use of an integral flowmeter (which the pressure sensors 152a, 152b can effectively be) and electronic actuation can ensure that the inhaler 100 can be actuated at an appropriate time in the patient's inspiratory maneuver. The electronic circuitry involved can also be configured to allow each triggering event to be counted and recorded, and can be used to also provide a dose count, e.g. for display to the patient of the theoretical number of doses thus still remaining.

As well as using the pressure measurements and the calculated flow rate data to trigger canister actuation (i.e., dose release firing), such a system can optionally be configured to provide feedback to the patient and to their physician.

The air flow path 146 containing the flow governor 140 can be incorporated, in a similar fashion as already described, into any of the variety of inhalers mentioned above. It should also be understood that the dedicated air flow path 146 is shown by way of example only, and that in some embodiments, an air inlet can be formed in an upper portion of the housing 55, and the flow governor 140 can be positioned in fluid communication with such an air inlet to govern air flow rates through the inhaler 100. For example, in some embodiments, the flow governor 140 can be positioned in a cap that is coupled to an open upper end of the housing 55.

In some embodiments, no matter which type of inhaler is employed, the air flow path 146 including the flow governor 140 and one or more of the pressure sensors 152a, 152b, the controller 151, and any other relevant electrical components, can be manufactured as a separate part or component, or as a portion of the inhaler 100. Exemplary flow governor assemblies comprising flow governors that can be separately formed and put in fluid communication with or otherwise incorporated into an inhaler, or that can form a portion of an inhaler of the present disclosure, are described in greater detail in PCT Publication No. WO2017/112748.

Auto-Reset Dose Release Firing System

Figure 19:
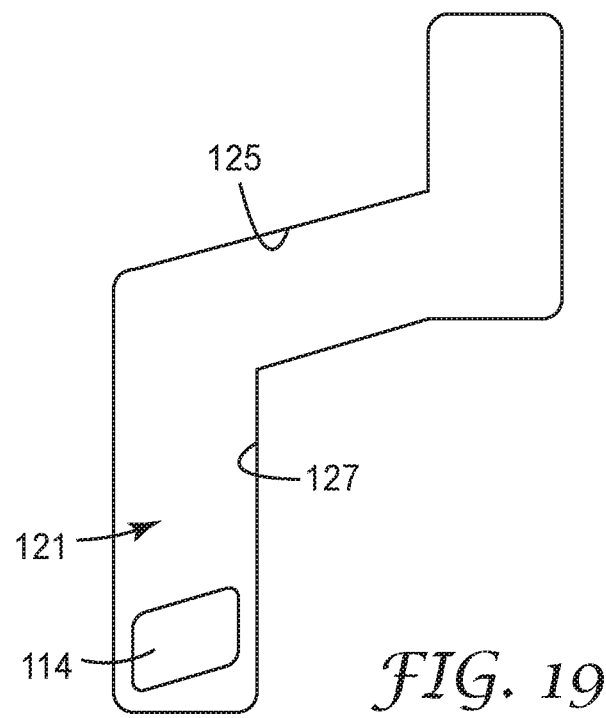
FIG. 19 is a schematic side 'un-rolled' flat view of the guideway of FIGS. 4, 5, 8-9, 15-16 and 18, the projection of FIGS. 3, 6-9, 15-16 and 18 shown positioned in the guideway in a second position, when the firing system of FIGS. 1-3, 15 and 17-18 is in its fired state.
Figure 20:
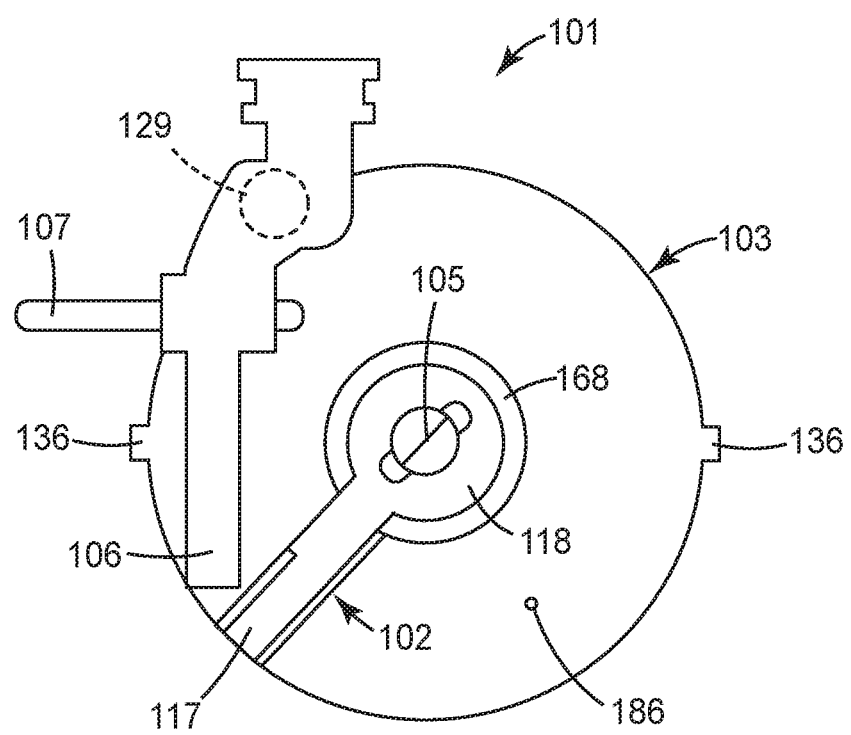
FIG. 20 is a top plan view of the firing system of FIGS. 1-3, 15 and 17-18 when in its fired state.
Figure 21:
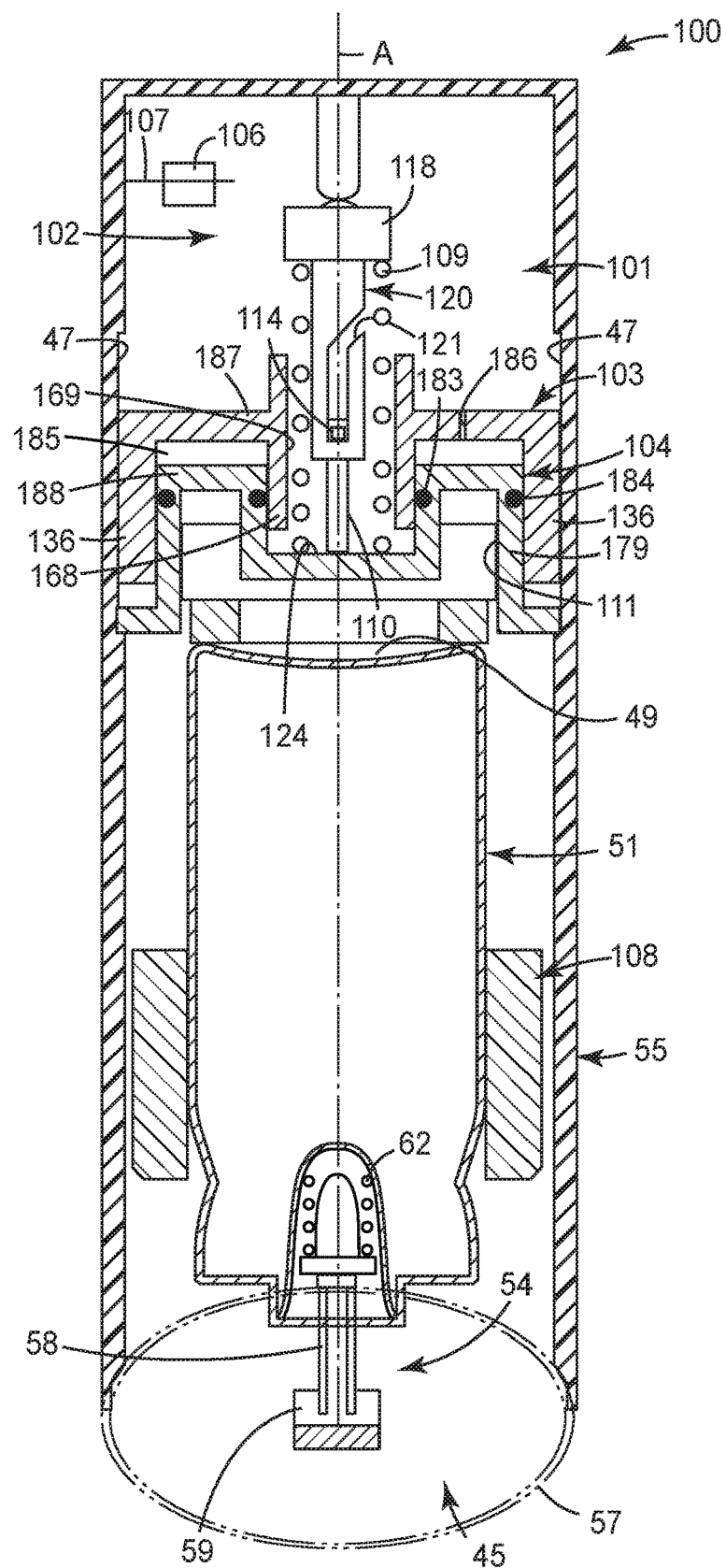
FIG. 21 is a schematic side cross-sectional view of the medicinal inhaler of FIGS. 1, 15 and 18, shown in the same orientation as FIGS. 15 and 18, the firing system being shown in a state intermediate between its fired state and its returned or reset state.
Figure 22:
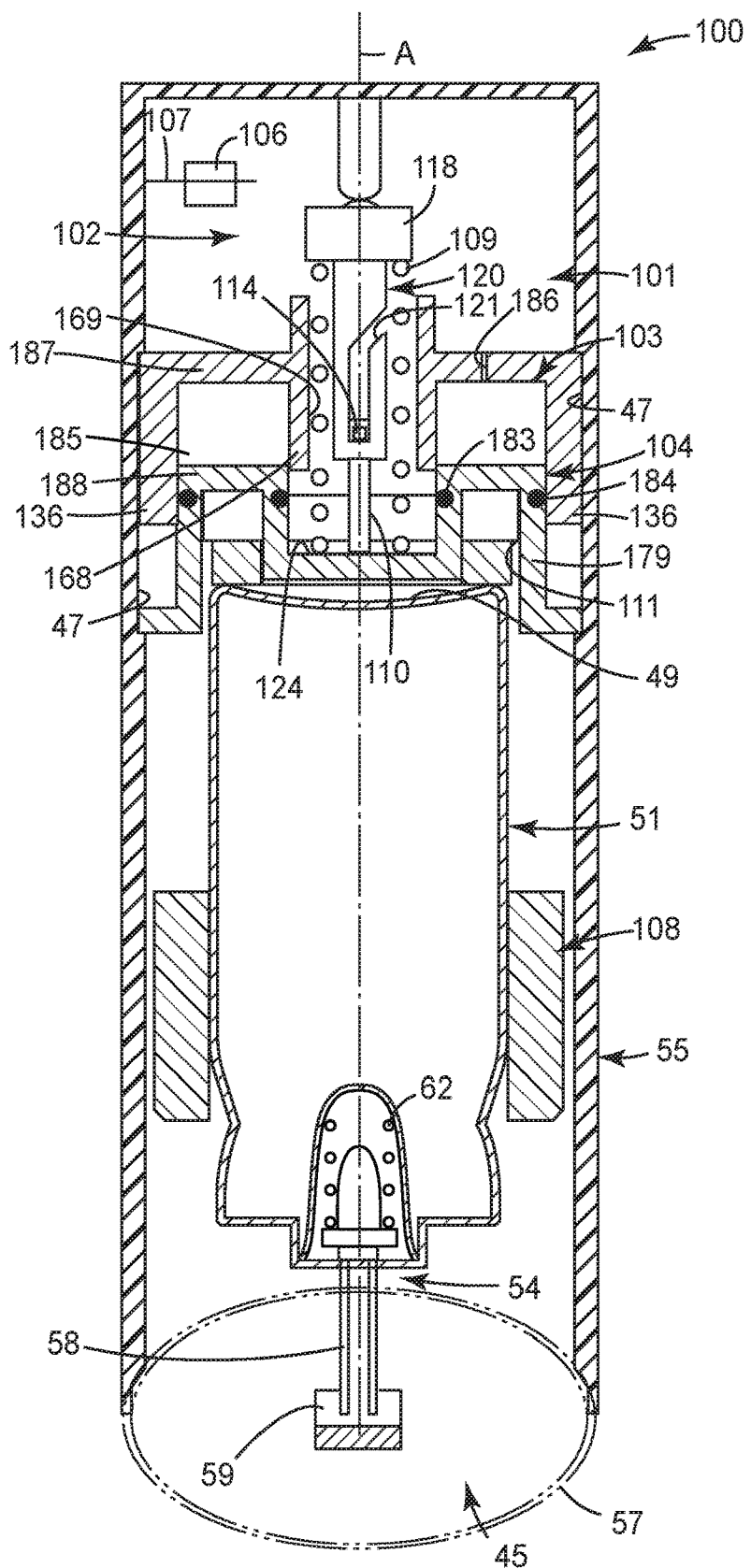
FIG. 22 is a schematic side cross-sectional view of the medicinal inhaler of FIGS. 1, 15, 18 and 21, shown in the same orientation as FIGS. 15, 18 and 21, the firing system being shown in its returned or reset state.

As mentioned above, FIGS. 2-22 illustrate various details of the auto-reset dose release firing system 101. FIGS. 1-3, 8 and 15-17 show aspects of the auto-reset dose release firing system 101 in a primed state, FIGS. 9, 18-20 show aspects the firing system 101 in a fired state, FIG. 21 shows the firing system 101 between being fired and reset, and FIG. 22 shows the firing system 101 in a returned or reset state.

The firing system 101 includes an axis (e.g., a longitudinal axis) A (see FIGS. 1-3); a rotary arm module 102 rotatable about the axis A; a first (e.g., outer) plunger 103, configured to be operatively coupled to the medicament canister 51, which is movable along, or parallel to, the axis A between a first (e.g., starting or primed) position, a second (e.g., fired) position, and a third (e.g., reset or returned) position (in some embodiments, the third position being the same as the first position); a second (e.g., inner) plunger 104 that is not configured to be coupled to the canister 51 and that is movable along, or parallel to, the axis A (e.g., coaxial with the first plunger 103) between a first (e.g., starting or primed) position and a second (e.g., fired) position; a convex circular spacer 105; a latch 106 pivotal about a pin 107, which can be connected to the inhaler housing 55 (see, e.g., FIG. 15); a firing pin 110; and a stored energy device 109 configured (and positioned relative to the second plunger 104) to drive the second plunger 104 from the first position to the second position when stored energy in the stored energy device is released.

The firing system 101 can be referred to as being primed (or cocked) or in a primed (or cocked) state when stored energy in the stored energy device 109 is not released and as being fired or in a fired state when the stored energy is released.

It should be noted that the inhaler 100 of FIG. 1 is a pressurized metered dose inhaler (pMDI), and that the firing system 101 operates to release a dose from the inhaler 100 by actuating the valve 54 of the canister 51. Particularly, the stem portion 58 of the valve 54 is held stationary relative to the housing 55 by the stem socket 59, and the can 53 is movable with respect to the valve 54, such that the canister 51 can be described as being movable in the axial direction (e.g., along the axis A) in response to the movement of the first plunger 103 to cause a dose to be released from the inhaler 100. However, as mentioned above, the firing system 101 can be employed in a variety of inhalers, and need not be employed in a pMDI. As a result, in embodiments in which the firing system 101 is employed in a different type of inhaler that does not employ the canister 51, the first plunger 103 need not be configured to be operatively coupled to the canister 51.

In some embodiments, the first stored energy device 109 can include a biasing element (e.g., a spring), which is shown as a coil spring, and particularly, a compression spring, by way of example only in the illustrated embodiment. However, stored energy devices of the present disclosure can include, but are not limited to, one or more of biasing elements (e.g., springs), propellants, chemicals, motors, electrical devices, and combinations thereof. In embodiments in which the stored energy device 109 includes a biasing element, the firing system 101 can be held under load, e.g., against the bias of the biasing element, when in its primed state.

The stored energy device 109 is configured such that the force provided by the energy released from the stored energy device 109 is sufficient to overcome any force necessary to actuate the canister valve 54, e.g., the spring force in the pMDI canister valve 54 of FIG. 1. For example, in some embodiments, the stored energy device 109 can provide at least 40 N in its unreleased (e.g., compressed state), i.e., with the device 'cocked' ready to trigger, in order to provide adequate force to operate the valve 54 (i.e., to move it to its firing position). That is, in some embodiments, the stored energy device 109 can provide at least 40 N of force when the stored energy is released; in some embodiments, at least 50 N; and in some embodiments, at least 60 N.

As described in greater detail below, driving the second plunger 104 to its second position (e.g., by the stored energy device 109) also causes the first plunger 103 to be driven to its second position, such that the first plunger 103 and the second plunger 104 are movable together from their first positions to their second positions. The first plunger 103 is further movable separately and independently from the second plunger 104 to its third position to allow the valve 54 to reset, i.e., automatically, after a desired time delay after firing.

Figure 2A:
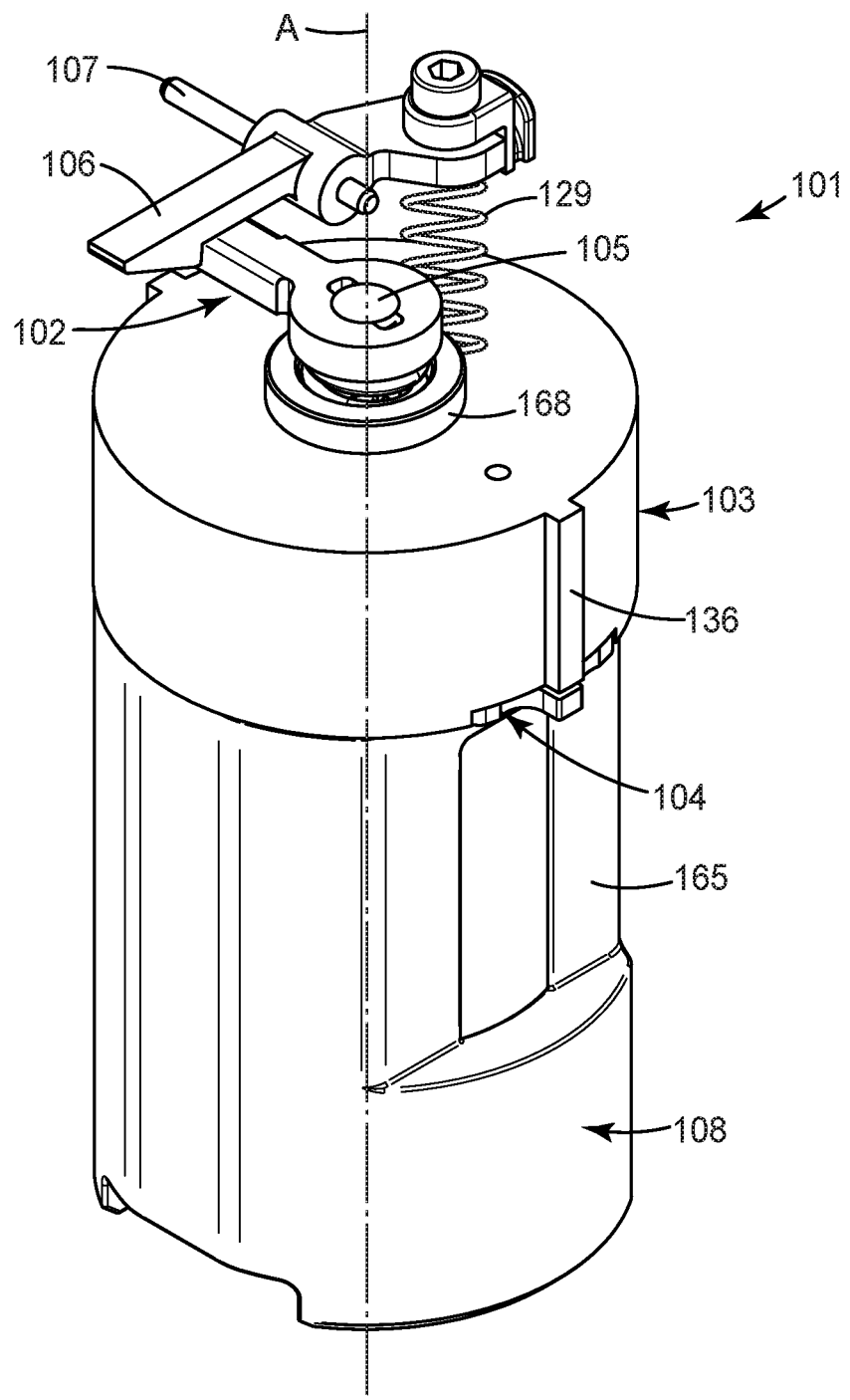
FIG. 2A is a top isometric view of the firing system of FIG. 1.
Figure 2B:
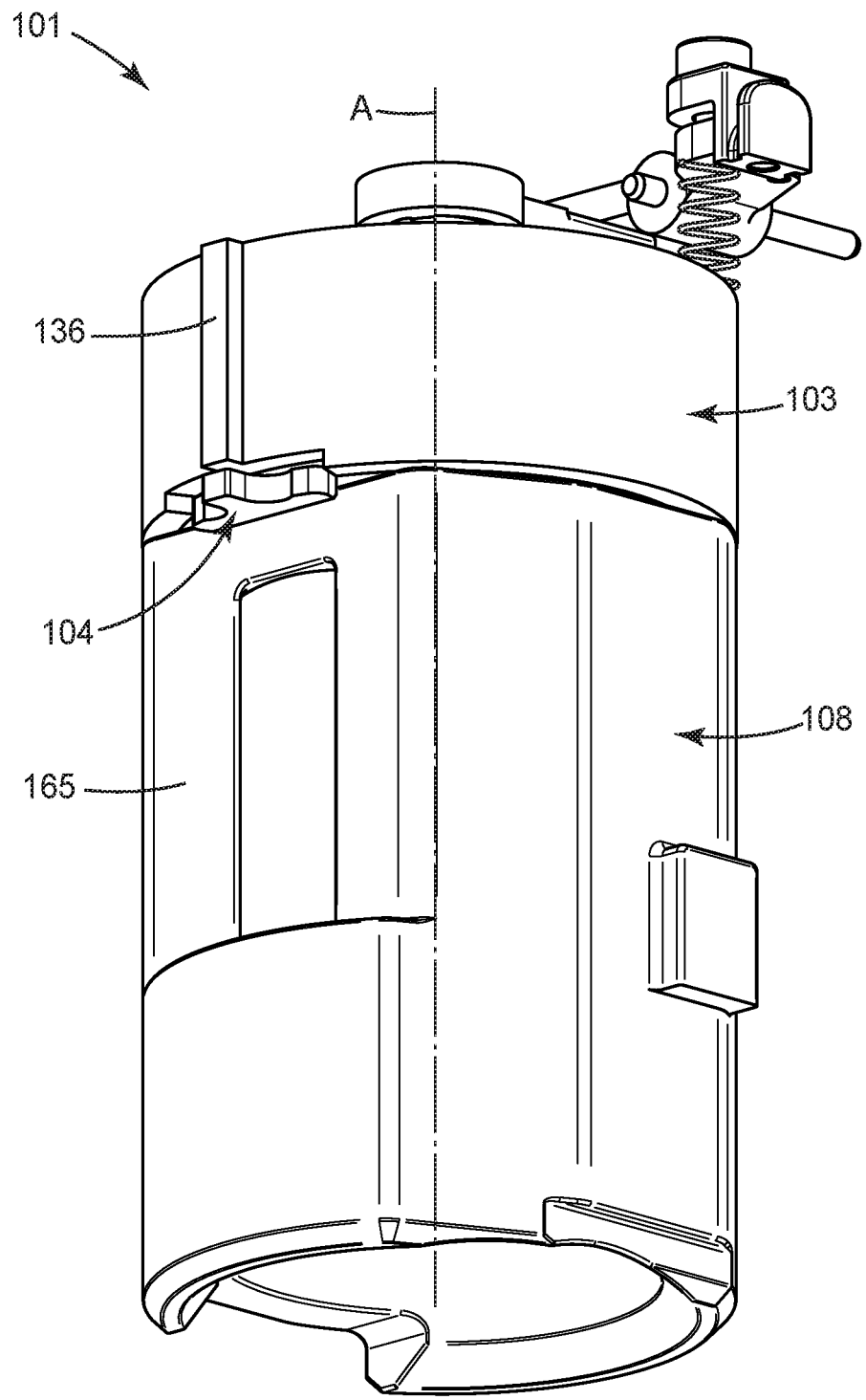
FIG. 2B is a bottom isometric view of the firing system of FIGS. 1 and 2A.

As shown, the plungers 103 and 104 are movable in the axial direction (e.g., along the axis A) with respect to the housing 55 and the canister 51 (i.e., in the inhaler 100, aligned with or parallel to a longitudinal direction of the canister 51) between a first (longitudinal or axial) position (e.g., a primed position) and a second (longitudinal or axial) position (e.g., a fired position) to actuate the dose release valve 54 of the canister 51. That is, the plungers 103 and 104 can be configured to move the medicament canister 51 along its longitudinal axis B (see FIG. 1) between a first position in which a medicament dose is not released and a second position in which a medicament dose is released, respectively. In addition, the plungers 103 and 104 can be rotationally fixed (e.g., with respect to the housing 55) about the axis A. For example, in some embodiments, at least one of the first plunger 103 and the second plunger 104 can include inter-engaging features with the housing 55 that inhibit the plunger(s) 103 and/or 104 and the housing 55 from rotating relative to one another about the axis A. In embodiments in which only one plunger 103 or 104 is inter-engaged with the housing 55, the plungers 103 and 104 can include inter-engaging features with one another that inhibit relative rotational movement about the axis A. By way of example, as shown in FIGS. 2A and 2B, in some embodiments, the first plunger 103 can include one or more ribs 136 (see FIGS. 2A, 2B, 3, 15, 17, 18 and 20), e.g., a set of diametrically-opposed ribs 136, each dimensioned to be received in a mating recess 47 (see FIGS. 15 and 18) formed in an inner surface of the housing 55, or vice versa. That is, in some embodiments, the first plunger 103 can alternatively or additionally include one or more recesses dimensioned to receive one or more ribs or projections from the housing 55. Additionally, or alternatively, in some embodiments, the second plunger 104 can include inter-engaging features with the housing 55.

The first plunger 103, the second plunger 104, and the adapter 108 will now be described in greater detail with reference to FIGS. 2A, 2B, 3 and 10-14.

As mentioned above, the first plunger 103 is configured to be operatively coupled to the canister 51, and the second plunger 104 is not. The adapter 108 is configured to be coupled to and to retain at least a portion (e.g., a base 49—see FIGS. 1, 15 and 18) of the canister 51. As such, the first plunger 103 is configured to be coupled to, and to therefore travel axially with, the adapter 108 (and therefore, the canister 51). However, while the second plunger 104 is dimensioned to receive at least a portion of the adapter 108 (and optionally the canister 51), such that the adapter 108 (and the canister 51) can move relative to the second plunger 104, the second plunger 104 is not configured to be coupled to, or to travel in the axial direction with, the adapter 108 (or the canister 51). This relative configuration or arrangement of the first plunger 103, the second plunger 104, and the adapter 108 is shown in FIGS. 2B and 3.

Figure 3:
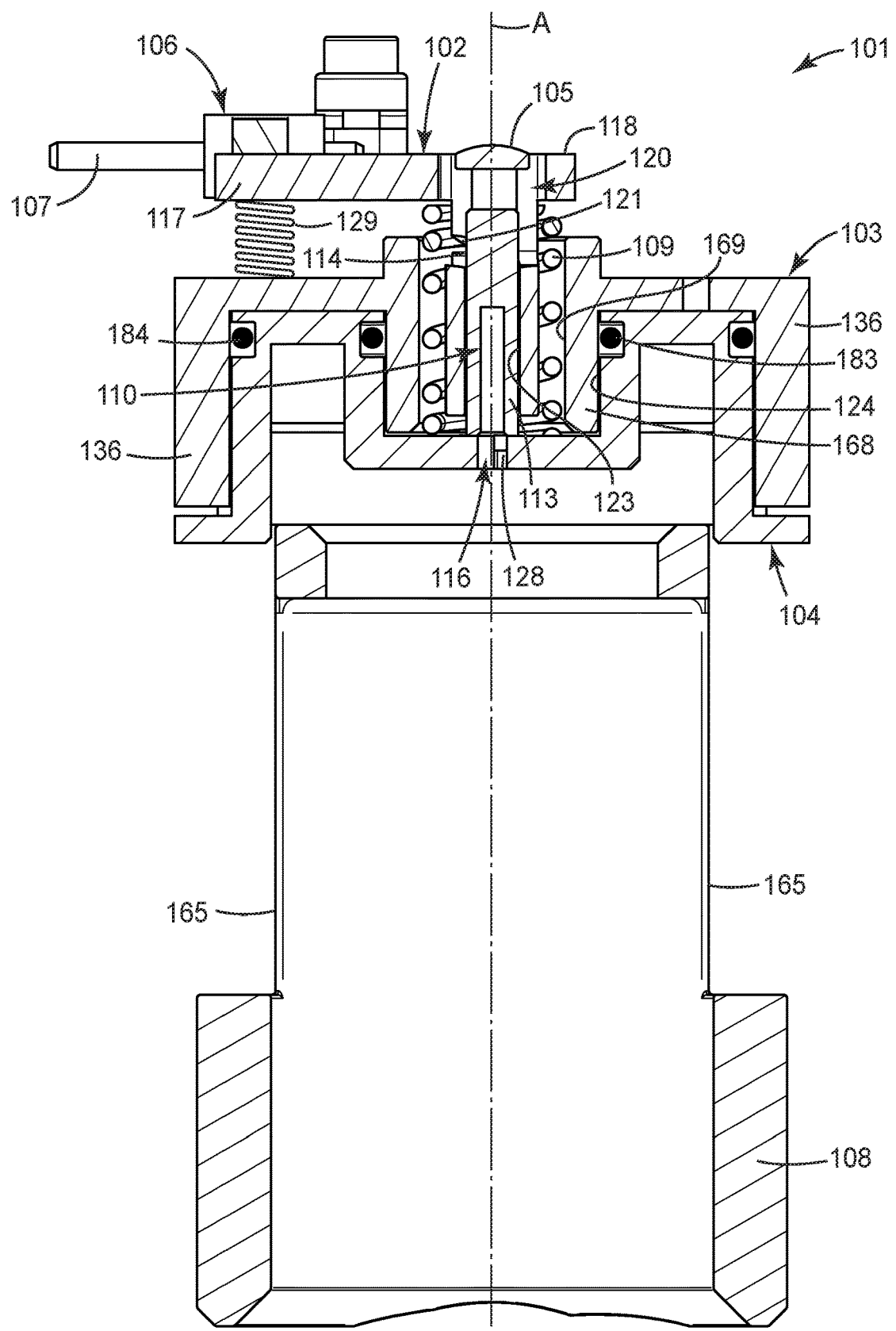
FIG. 3 is a side cross-sectional view of the firing system of FIGS. 1, 2A and 2B, shown rotated 90 degrees about a longitudinal axis relative to the side view shown in FIG. 1, the firing system comprising a firing pin, a rotary arm module, a first plunger, a second plunger, and an adapter.

As shown in FIG. 3, in some embodiments the second plunger 104 can include a first (e.g., lower) recess (or outer channel) 111 dimensioned to receive at least a portion of the adapter 108, and possibly therefore also at least a portion of the canister 51 (e.g., at least a portion of the base 49 of the canister 51, opposite the end comprising the dose release valve 54). As shown in FIG. 3, the first recess 111 can be annular in shape and can be downwardly-facing, i.e., opening toward a medicament canister (e.g., the canister 51) of a medicinal inhaler.

The adapter 108 can be configured, i.e., shaped and dimensioned, to allow the canister 51 to be operatively coupled to the first plunger 103 and not the second plunger 104. As shown in FIGS. 2A, 2B, 3 and 14, the adapter 108 can include an approximately cylindrical shape that is predominantly hollow. The adaptor 108 can include one or more recessed flat surfaces 165 (e.g., two diametrically-opposed flat surfaces 165) that allow at least an upper portion of the adapter 108 to be received in the first recess 111 of the second plunger 104 and to move relative to the second plunger 104 (i.e., up into the recess 111). In some embodiments, the recessed flat surface 165 can extend approximately two-thirds of the way down the height of the adaptor 108. However, the regions of the outer surface of the adapter 108 that do not include the flat surface 165 can be configured to abut a lower portion or surface of the first plunger 103 (see FIGS. 2B and 3), such that as the first plunger 103 moves in the axial direction (e.g., along the axis A), it abuts the adapter 108 (e.g., is coupled to the adapter 108), causing the adapter 108 (and the canister 51) to move accordingly.

Figure 14:
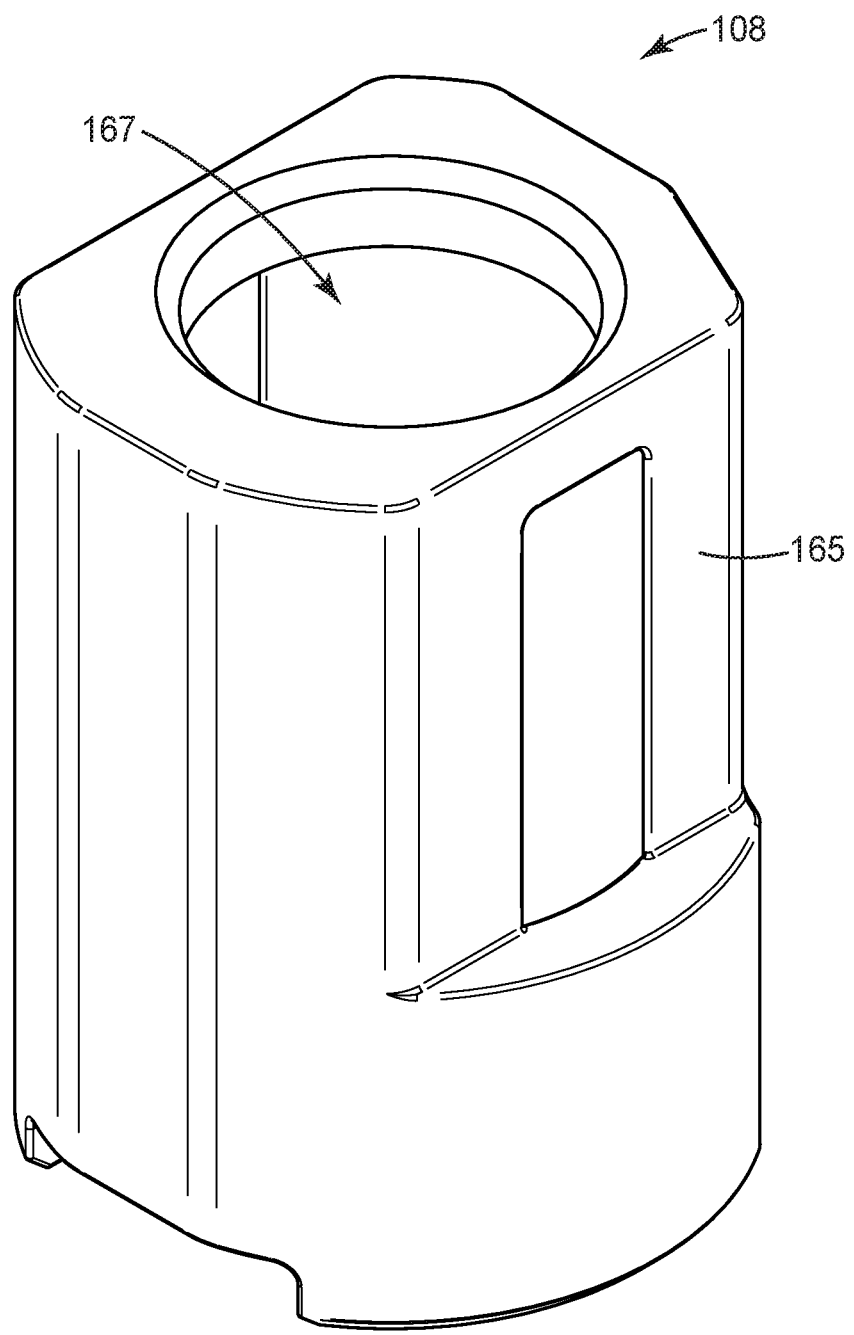
FIG. 14 is a top isometric view of the adapter of the firing system of FIGS. 1-3.

As further shown in FIG. 14, the hollow adapter 108 can include an opening 167 in its upper surface that is dimensioned to receive at least a portion of the first plunger 103, the second plunger 104, the stored energy device 109, the rotary arm module 102, and the firing pin 110 (see FIG. 3).

The first plunger 103 and the second plunger 104 can be configured such that at least one of the first plunger 103 and the second plunger 104 is dimensioned to receive at least a portion of the other of the first plunger 103 and the second plunger 104. In some embodiments, as shown in FIG. 3, each of the first plunger 103 and the second plunger 104 can be configured to receive at least a portion of the other, such that the first plunger 103 and the second plunger 104 include inter-engaging structures.

As further shown in FIG. 3, in some embodiments, the second plunger 104 can include a second (e.g., upper) recess 124 dimensioned to receive at least a portion of the first plunger 103, the rotary arm module 102, the firing pin 110, and the stored energy device 109. In some embodiments, as shown, the second recess 124 can be centrally located and can have a tubular shape and/or can be cup-like. As shown, at least a portion of the first recess 111 of the second plunger 104 can be located radially outwardly of the portion of the second plunger 104 that includes or defines the second recess 124. As a result, the second plunger 104 can include a central, downwardly-projecting (e.g., tubular) portion (or tubular projection) 163 (i.e., that includes the second recess 124) and an outer upwardly-projecting annular portion (or annular projection) 166 (i.e., that includes the first recess 111)—see FIGS. 12 and 13. The tubular projection 163 and the annular projection 166 can each project axially along or substantially parallel to the axis A. The tubular projection 163 can project axially toward a medicament canister of a medicinal inhaler (e.g., the canister 51), and the annular projection 166 can project axially away from the medicament canister.

Figure 11:
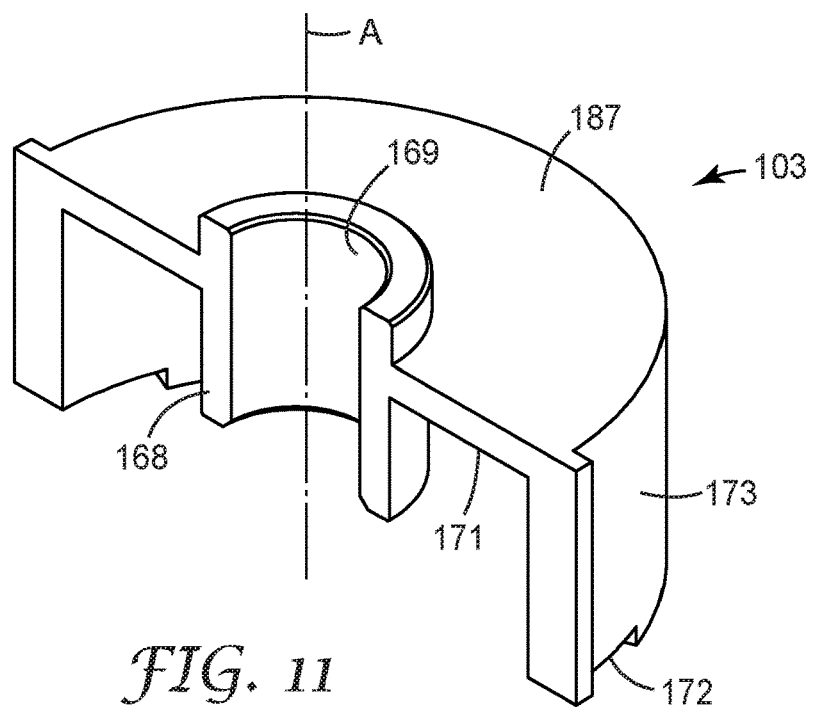
FIG. 11 is a side isometric cross-sectional view of the first plunger of FIG. 10.

Correspondingly, as shown in FIGS. 3 and 11, the first plunger 103 can include a tubular projection 168 dimensioned to be received in the second recess 124 of the second plunger 104, and an (outer) annular recess 171 dimensioned to receive the annular projection 166 of the second plunger 104. The tubular projection 168 can be centrally located (e.g., along the axis A) and can be hollow, defining an inner tubular channel 169 dimensioned to receive at least a portion of the stored energy device 109, the rotary arm module 102, and the firing pin 110.

The tubular projection 168 can project axially and particularly, can extend downwardly, i.e., toward a medicament canister of the medicinal inhaler. The annular recess 171 of the first plunger 103 can be formed between the tubular projection 168 and an outer sleeve portion 173 of the first plunger 103. As a result, the outer sleeve portion 173 of the first plunger 103 can be described as being dimensioned to receive at least a portion of the second plunger 104. As shown in FIGS. 1, 2A and 2B, the first plunger 103 and the second plunger 104 can be configured such that the second plunger 104 is substantially enveloped by the first plunger 103.

Figure 10:
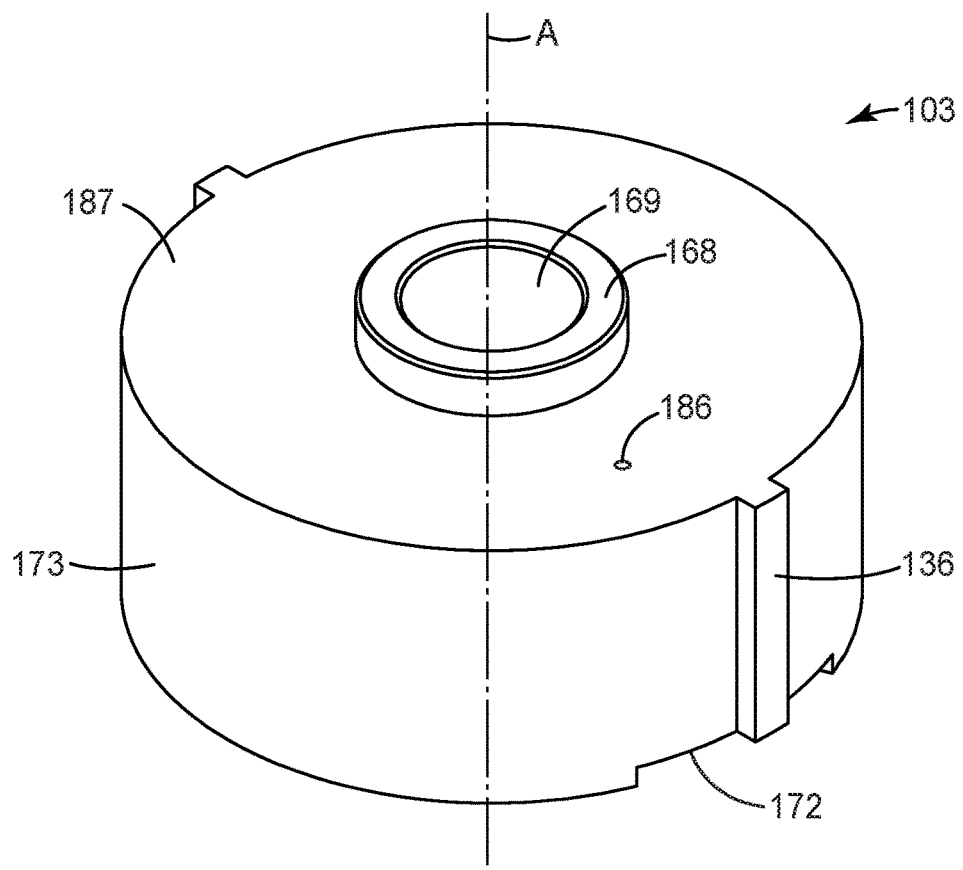
FIG. 10 is a top isometric view of the first plunger of the firing system of FIGS. 1-3.

The tubular projection 168 can also extend or project upwardly to form a raised circular profile on the top surface of the first plunger 103 (see FIGS. 10 and 11). The lower portion of the tubular projection 168 extends axially downwardly approximately halfway into the outer annular recess 171 of the first plunger 103.

The tubular channel 169 can be open-ended at its top and at its bottom to allow at least a portion of other components (e.g., the rotary arm module 102, the firing pin 110 and the stored energy device 109) to reside in the channel 169 while also being coupled to (e.g., in contact with) a base of the second recess 124 of the second plunger 104—i.e., being coupled to the tubular projection 163 of the second plunger 104.

With reference to FIGS. 10 and 11, the first plunger 103 can further include one or more notches or recesses 172 formed in a bottom surface of the outer sleeve portion 173, each of which can be located directly underneath the ribs 136. Two diametrically opposed notches 172 are shown by way of example only, and each rib 136 is centrally located with respect to each notch 172.

Figure 12:
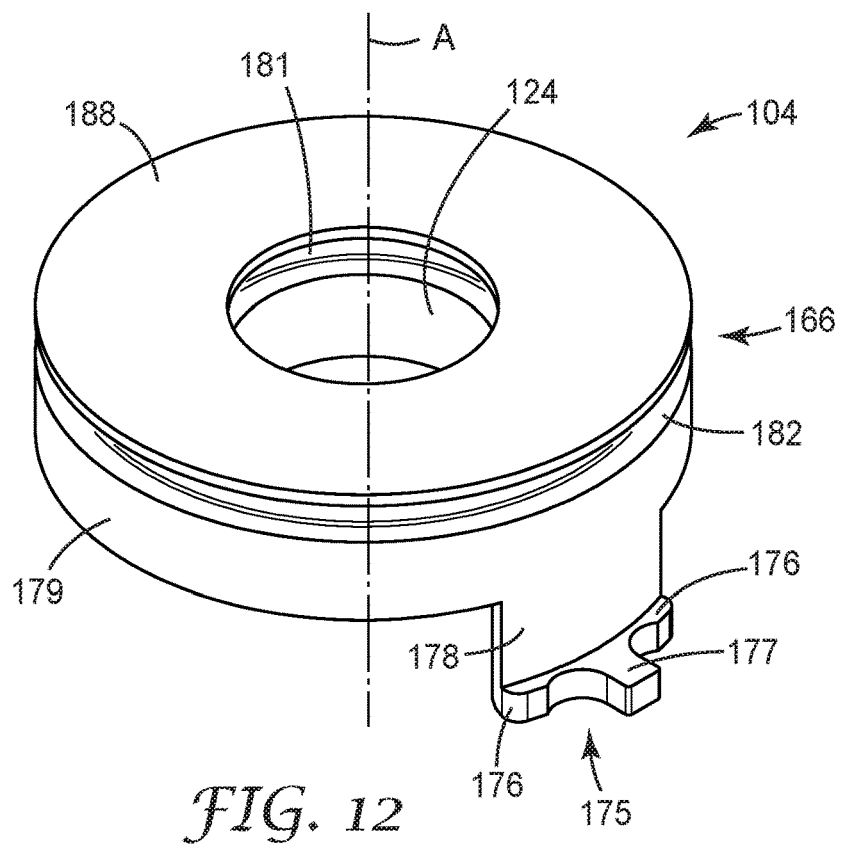
FIG. 12 is a top isometric view of the second plunger of the firing system of FIGS. 1-3.
Figure 13:
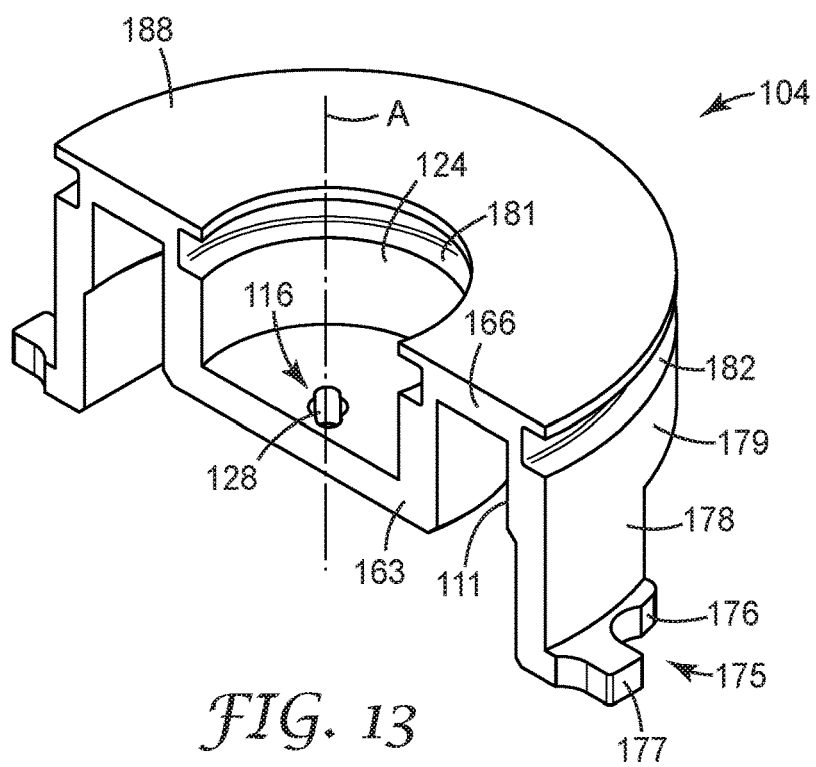
FIG. 13 is a side isometric cross-sectional view of the second plunger of FIG. 12.

Each notch 172 can be dimensioned to receive a radially outwardly extending projection (or radial projection) 175 of the second plunger 104 (see FIGS. 12 and 13). In some embodiments, as shown, each radially outwardly extending projection 175 can include three separate radial projections—two outer projections 176 and a central projection 177 that extends further radially than the outer projections 176. As shown in FIG. 2A, the central radial projection 177 can be aligned generally with the ribs 136 of the first plunger 103, and can be configured to inter-engage with the housing 55 in a similar manner as the ribs 136 of the first plunger 103 to additionally rotationally fix the second plunger 104 to the housing 55.

In some embodiments, as shown in FIGS. 12 and 13, the radial projection 175 of the second plunger 104 can extend radially from (i.e., be coupled to) an axially projecting arm 178 that can extend axially downwardly from an outer tubular sleeve portion 179 that forms a portion of the annular projection 166 and defines at least a portion of the first recess 111. By way of example only, the second plunger 104 can include two arms 178 that are diametrically opposed.

The first plunger 103 and the second plunger 104 are movable axially with respect to one another, such that the first plunger 103 and the second plunger 104 are separately and independently movable in the axial direction (e.g., along the axis A). As a result of this independent movement, the first plunger 103 and the second plunger 104 can form an evacuable chamber 185 therebetween (i.e., when the first and second plungers 103 and 104 are assembled; see FIGS. 21 and 22, which will be described in greater detail below). The evacuable chamber 185 can be defined between an underside of an upper wall or surface 187 of the first plunger 103 (and particularly, the annular recess 171) and an upper wall or surface 188 of the second plunger 104 (and particularly, the annular projection 166).

As shown in FIG. 10, the first plunger 103 can include a vent (or vent hole) 186 formed through an upper surface thereof, such that the vent 186 is in fluid communication with the evacuable chamber 185 (i.e., when the first and second plungers 103 and 104 are assembled). The vent 186 can be dimensioned such that the chamber 185 can be evacuated, at least temporarily (e.g., when the first plunger 103 and the second plunger 104 are moved from the first position to the second position), and the rate of air ingress back into the chamber 185 via the vent 186 can be controlled by controlling the dimensions of the vent 186, the air ingress, e.g., moving the first plunger 103 from its second position to its third, reset, position. Generally, the larger the diameter (or cross-dimension if non-circular) of the vent 186, or the larger the collective cross-sectional area if multiple vents 186 are employed, the faster air will move into the chamber 185, the faster the first plunger 103 will move to its third position, and the faster the canister valve 54 will reset. In some embodiments, the vent 186 can have a diameter (or cross-dimension if a non-circular vent is employed) of no greater than 100 micrometers.

Although FIG. 10 illustrates vent 186 formed through an upper surface of the first plunger 103, it will be obvious to one skilled in the art that the vent 186 could additionally or alternatively be formed through the second plunger 104. Additionally, it is possible to have more than one vent 186. Additionally, the vent 186 need not be an open channel. In some embodiments, a porous membrane (e.g., a low density open cell foam) could cover an opening of the vent 186, or occupy part or all of the channel of the vent 186. Inclusion of such a porous membrane can inhibit the vent 186 from becoming blocked by debris. As a further alternative, an air leakage path can be provided using a small groove (e.g., vertically up the inside of the outer sleeve portion 173 of the first plunger 103) rather than a hole or channel formed through a horizontal surface.

As shown in FIGS. 12 and 13, the second plunger 104 can further include an inner channel 181 and an outer channel 182. Each channel 181, 182 can be dimensioned to retain a seal or sealing member, e.g., an annular seal, such as an O-ring (shown in FIG. 3, but not shown in FIGS. 12 and 13). Particularly, the inner channel 181 can retain a first seal 183, and the outer channel 182 can retain a second seal 184 (see FIG. 3). As such, the evacuable chamber 185 formed between the first plunger 103 and the second plunger 104 can be air-tight, except for the vent hole 186.

The first and second seals 183 and 184 can be formed of any suitable material, having any suitable cross sectional shape to form an air-tight seal between the first plunger 103 and the second plunger 104. The two seals 183 and 184 can be formed of different materials from one another, and can have different cross-sectional shapes from one another. In some embodiments, each of the first and second seals 183 and 184 can be elastomeric (e.g., formed from a rubber or from a thermoplastic elastomer). In some embodiments, the first and second seals 183 and 184 are both formed of a nitrile rubber. In some embodiments, each of the first and second seals 183 and 184 is an O-ring with a circular cross-sectional shape. Alternatively, in some embodiments, the first and second seals 183 and 184 may take the form of annular lip seals.

Figure 4:
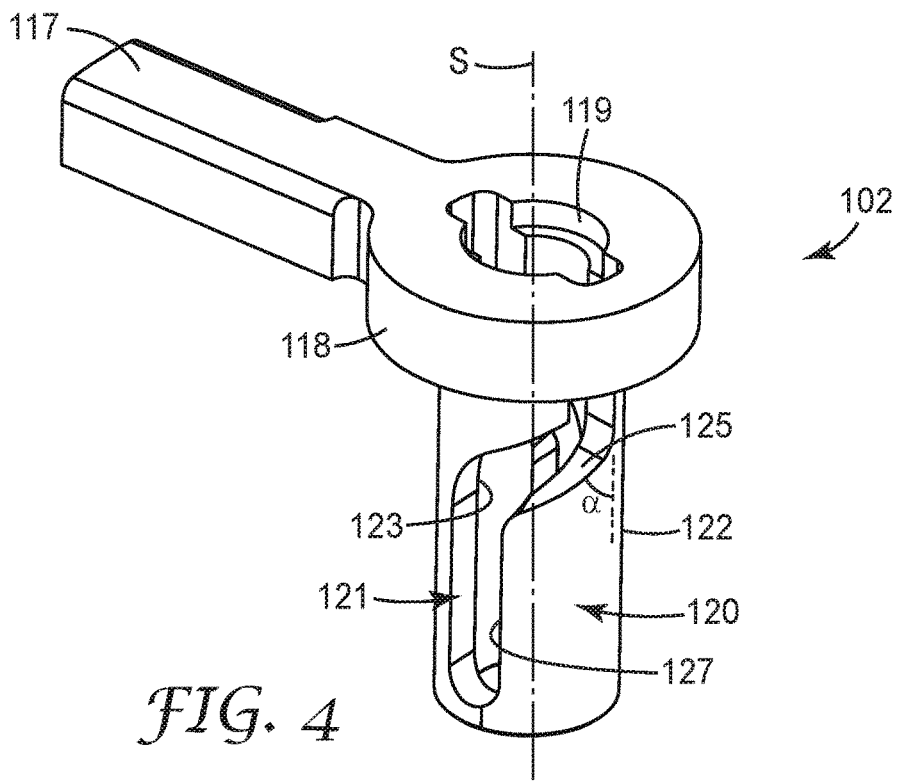
FIG. 4 is a top isometric view of the rotary arm module of the firing system of FIGS. 1-3, the rotary arm module comprising a guideway.
Figure 5:
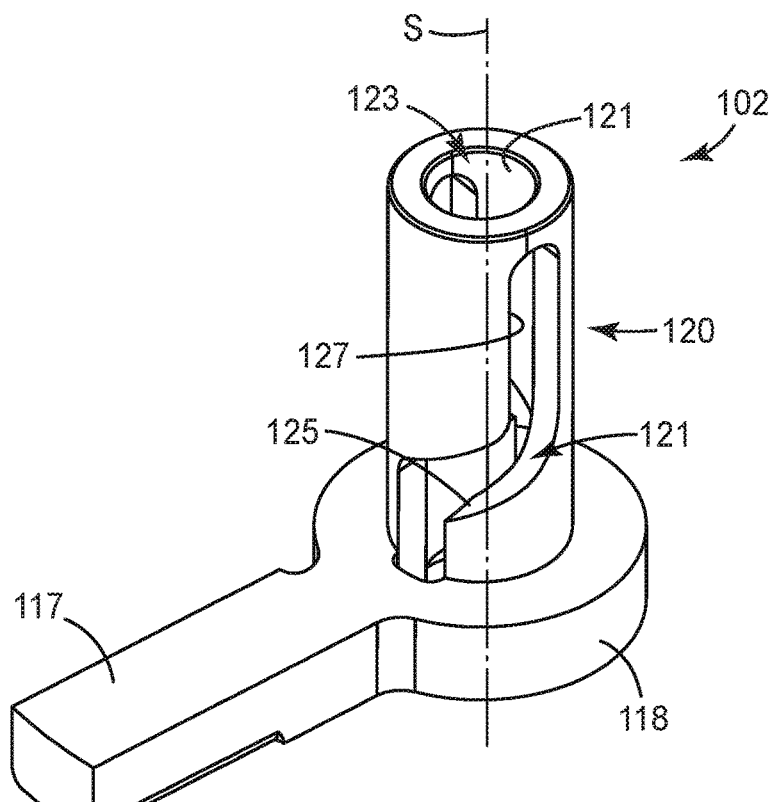
FIG. 5 is a bottom isometric view of the rotary arm module of FIG. 4.
Figure 6:
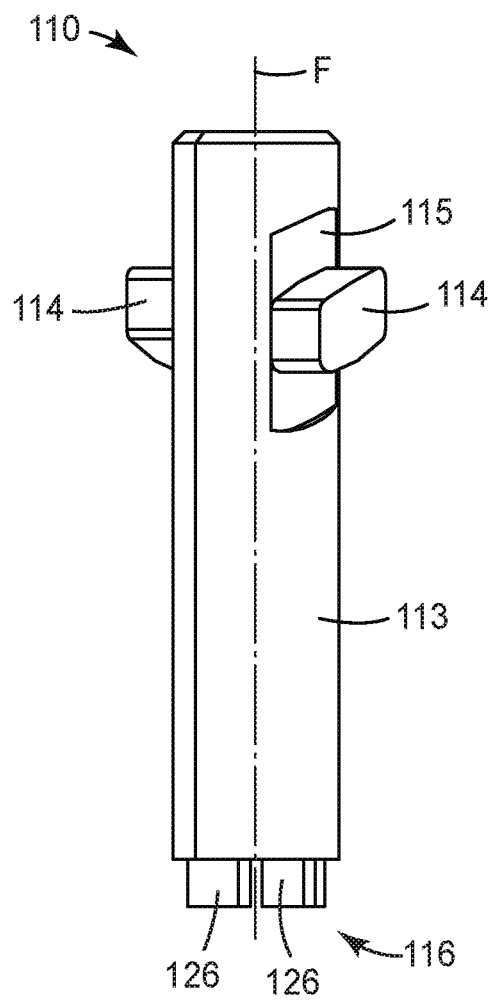
FIG. 6 is an isometric view of the firing pin of the firing system of FIGS. 1-3, the firing pin comprising a projection dimensioned to be received in the guideway of the rotary arm module.
Figure 7:
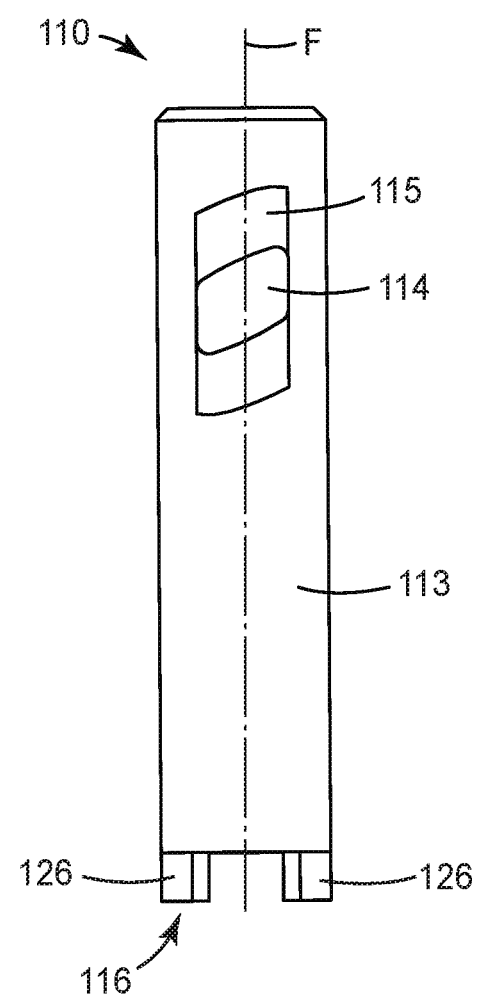
FIG. 7 is a side elevational view of the firing pin of FIG. 6.
Figure 8:
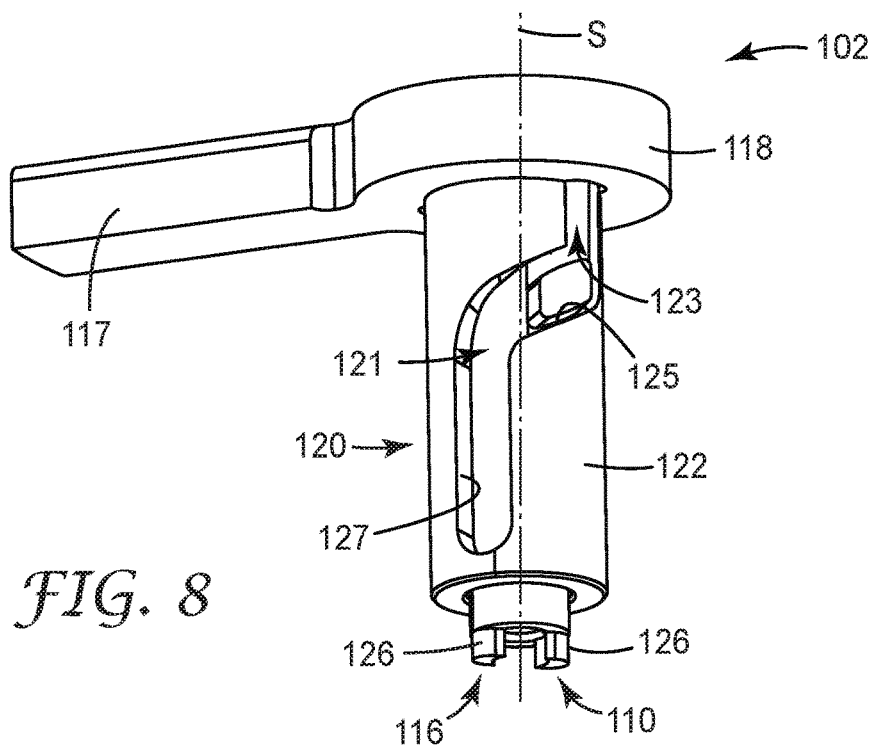
FIG. 8 is an isometric view of the rotary arm module of FIGS. 4 and 5 and the firing pin of FIGS. 6 and 7, assembled, the firing pin shown in a first position with respect to the rotary arm module, such that the projection is shown in a first position with respect to the guideway.
Figure 9:
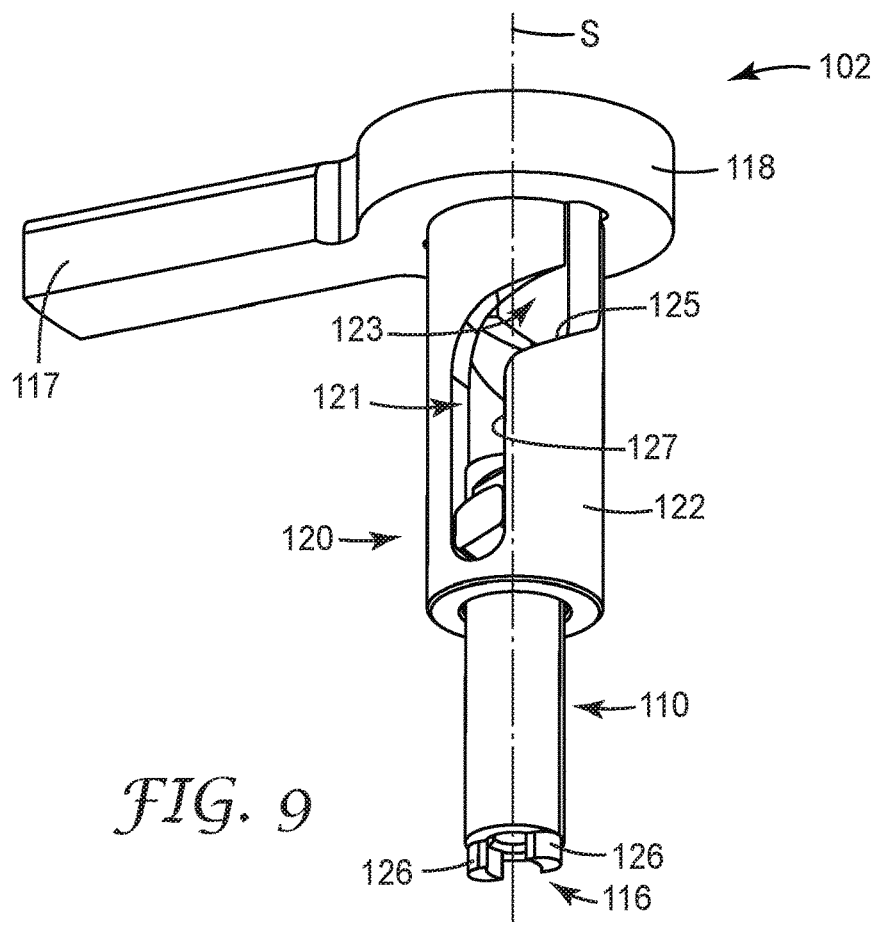
FIG. 9 is an isometric view of the rotary arm module of FIGS. 4, 5 and 8 and the firing pin of FIGS. 6-8, assembled, the firing pin shown in a second position with respect to the rotary arm module, such that the projection is shown in a second position with respect to the guideway.

FIGS. 4-5 illustrate the rotary arm module 102 in greater detail; FIGS. 6-7 illustrate the firing pin 110 in greater detail; and FIGS. 8-9 illustrate in greater detail how the rotary arm module 102 and the firing pin 110 interact.

The rotary arm module 102 is shown and described herein as one example for providing a guideway 121 of the present disclosure. The firing pin 110, at least a portion of which is dimensioned to be received within the rotary arm module 102, is shown and described herein as one example for providing a projection 114 of the present disclosure dimensioned to be received in and movable in the guideway 121. However, it should be understood that other suitable structures can be employed for providing the guideway 121 and the projection 114 of the present disclosure. As mentioned above, either the guideway 121 or the projection 114 can be fixedly coupled to the second plunger 104, and in some embodiments, can be integrally formed with the second plunger 104. The guideway 121 and the projection 114 can be rotatable with respect to one another about the axis A, and can be further translatable with respect to one another along, or substantially parallel to, the axis A. In the embodiment illustrated in FIGS. 2-22, the firing pin 110 includes the projection 114 and is fixedly coupled to the second plunger 104, and the rotary arm module 102 (and accordingly, the guideway 121) is rotatable about the axis A relative to the second plunger 104 (and relative to the firing pin 110, and accordingly, the projection 114). In addition, the rotary arm module 102 and the second plunger 104 (along with the firing pin 110, and therefore, the projection 114) are movable (i.e., translatable) with respect to one another in the axial direction (e.g., parallel with the axis A), e.g., at least when the projection 114 is in the second portion 127 of the guideway 121.

In some embodiments, as shown, the guideway 121 can include a two-sided channel or groove, e.g., with walls spaced a distance apart to be dimensioned to receive the projection 114 therebetween.

However, it should be understood that this need not be the case. For example, in some embodiments, the guideway 121 can be fixedly coupled to the second plunger 104 (e.g., via the firing pin 110, another suitable structure, or by being integrally formed therewith), and the projection 114 can be provided by (e.g., coupled to or integrally formed with) the rotary arm module 102 or another suitable structure. In such embodiments, the guideway 121 and the projection 114 would still be rotatable and translatable with respect to one another in order to move the second plunger 104 from its first position to its second position to accordingly move the first plunger 103 from its first position to its second position to actuate dose release, e.g., to actuate the canister valve 54 in embodiments employing a pMDI canister, such as the embodiment shown in FIG. 1.

As a result of the at least temporary "vacuum" (i.e., the region from which the air has largely been driven) that is created in the evacuable chamber 185 between the first plunger 103 and the second plunger 104 when the firing system 101 is primed (e.g., and the first plunger 103 and the second plunger 104 are pressed toward one another), when the second plunger 104 is actuated to move from its first (e.g., starting or primed) position to its second (e.g., fired) position, the first plunger 103 is also pulled by the second plunger 104 from its first (e.g., starting or primed) position to its second (e.g., fired) position. That is, the first plunger 103 and the second plunger 104 are movable together from their respective first positions to their respective second positions as a result of the evacuable chamber 185 being evacuated in the primed state of the firing system 101, and the first plunger 103 is separately and independently movable to its third position as a result of air entering the evacuable chamber 185 via the vent 186.

Said another way, movement of the first plunger 103 from the first position to the second position is in response to a reduced pressure (i.e., a reduced air pressure relative to outside of the evacuable chamber 185, e.g., a "vacuum") being developed in the evacuable chamber 185 as a result of movement of the second plunger 104 from the first position to the second position, such that the first plunger 103 is essentially pulled down, or sucked down, by movement of the second plunger 104. (The first plunger 103 will also experience an additional downwards force from friction with the first and second seals 183 and 184 as the second plunger 104 moves down.)

As a result, when the first plunger 103 and second plunger 104 are in the first position and the second position, they essentially form one plunger that moves axially along axis A, e.g., with respect to a medicament canister (and housing) of an inhaler. However, the first plunger 103 and the second plunger 104 are independently movable with respect to one another and to the medicament canister (and the housing) of the inhaler when the first plunger 103 moves from its second position to its third position, due to air entering the evacuable chamber 185. The automatic reset function of the firing system 101, and the movement of the first plunger 103 from its second position to its third position is described in greater detail below with respect to FIGS. 21 and 22.

The rotary arm module 102, the firing pin 110, the guideway 121, and the projection 114 will now be described in greater detail with respect to FIGS. 4-9.

As shown in FIGS. 4-5, the rotary arm module 102 of the illustrated embodiment includes a shaft 120 having a shaft axis (e.g., a longitudinal axis) S configured to be oriented along or parallel to the axis A when the firing system 101 is assembled, and comprising a wall 122. The guideway 121 can be formed in the wall 122, and particularly, can be formed at least partially through the thickness of the wall 122, or can be formed all the way through the thickness of the wall 122 (i.e., as shown in FIGS. 4-5 and 8-9).

In some embodiments, more than one guideway 121 can be provided. For example, as shown, the shaft 120 of the rotary arm module 102 includes two guideways 121, and particularly, two diametrically opposed guideways 121. As few as one guideway 121 and as many as structurally possible and/or necessary for balanced, coordinated, and/or reliable operation of the firing system 101 can be employed. One guideway 121 will be described in greater detail for simplicity, but it should be understood that the description of the guideway 121 can be applied to as many guideways 121 as employed.

As shown in FIGS. 4-5 and 8-9, at least a portion of the guideway 121 can have a helical shape. That is, the guideway 121 can include a portion of a helix, but need not extend fully about 360 degrees of the shaft 120. For example, in some embodiments, the guideway 121 may only extend about the shaft 120 for less than 90 degrees; in some embodiments, less than 60 degrees; in some embodiments, less than 45 degrees; and in some embodiments, less than 40 degrees.

Particularly, as shown, the guideway 121 can have a first (e.g., upper) portion 125 having a first helix angle α (see FIG. 4) with respect to the axis A (or with respect to the shaft axis S) that is greater than zero. As a result, at least the first portion 125 is a helical portion of the guideway 121. Furthermore, the guideway 121 can have a second (e.g., lower) portion 127 having a second helix angle with respect to the shaft axis S (or the axis A when the firing system 101 is assembled) that is less than the first helix angle α. In the illustrated embodiment, the second helix angle is substantially zero and is therefore not indicated with a reference symbol or numeral. Because the second helix angle is substantially zero, the second portion 127 of the illustrated guideway 121 is substantially aligned with, or is oriented substantially parallel with respect to, the shaft axis S (and the axis A when the firing system 101 is assembled), and is not helical. As a result, in some embodiments, the guideway 121 can be described as including a first helical portion 125, and a second axial (or straight, or linear) portion 127.

Particularly, the second helix angle is less than the first helix angle α (i.e., the second portion 127 of the guideway 121 is oriented at a smaller angle with respect to the axis A than the first portion 125), such that the second portion 127 of the guideway 121 is steeper than the first portion 125 of the guideway 121. Said another way, the second portion 127 of the guideway 121 can be described as being more aligned with, or more parallel to, the axis A, or oriented more axially with respect to the axis A, than the first portion 125 of the guideway 121.

By employing a unique two-portion guideway 121 where the first portion 125 has a greater helix angle than the second portion 127, the guideway 121 can assist the latch 106 in holding back the relatively large firing force of the stored energy device 109 (e.g., the load of a spring), which can allow the use of a sensitive latch 106 where the entire force of the stored energy is not all placed directly on the latch 106 but still provides sufficient axial firing force (e.g., after the projection 114 has transitioned from the first portion 125 to the second portion 127 of the guideway 121.

In some embodiments, the first helix angle α can be at least 45 degrees, in some embodiments, at least 50 degrees, in some embodiments, at least 60 degrees, and in some embodiments, at least 65 degrees. In some embodiments, the first helix angle α can be less than 90 degrees, in some embodiments, less than 80 degrees, in some embodiments, less than 60 degrees, in some embodiments, less than 50 degrees, and in some embodiments, less than 45 degrees.

In some embodiments, the second helix angle can be less than 45 degrees, in some embodiments, less than 30 degrees, in some embodiments, less than 25 degrees, in some embodiments, less than 20 degrees, in some embodiments, less than 15 degrees, in some embodiments, less than 10 degrees, in some embodiments, less than 5 degrees, and in some embodiments, is about 0 degrees (i.e., such that the second portion is substantially axial and oriented substantially along or parallel to the axis).

In some embodiments, as shown, at least a portion of the guideway 121 (e.g., the first portion 125) can be curved. As a result, the first portion 125 of the guideway 121 may not have a constant first helix angle, but in such embodiments, any helix angle along the first portion 125 (as measured relative to the vertical, i.e., as measured relative to the axis A or the shaft axis S) is greater than the second helix angle. Alternatively, in such curved embodiments, the "first helix angle" can refer to an average helix angle over the curved first portion 125 of the guideway 121.

The shaft 120 can further include a flanged (upper) end 118, which can be in the form of an annular cylindrical flange and can include or define an orifice 119. In some embodiments, the shaft 120 can be hollow and can define a tubular channel 123 that extends along the shaft axis S. As such, the shaft 120, and particularly, the tubular channel 123 can be dimensioned to receive the firing pin 110. In such embodiments, the orifice 119 can be generally aligned with, and connected to, the tubular channel 123 of the shaft. The flanged end 118 of the shaft 120, and particularly the bottom surface thereof, can be configured to provide a surface against which the stored energy device 109 can press, e.g., when the stored energy device 109 is in the form of a biasing element. In such embodiments, the second recess 124 of the second plunger 104 (e.g., a base of the second recess 124) can provide the opposing surface against which the stored energy device 109 can press. The shaft 120 can be dimensioned to be received in the second recess 124 of the second plunger 104, along with the stored energy device 109 and the firing pin 110, and the shaft 120 can be rotatable about the shaft axis S (and about the axis A of the firing system 101 when assembled). The shaft 120, the stored energy device 109, and the firing pin 110 can also be received in the tubular channel 169 of the first plunger 103, as shown in FIG. 3. As such, the shaft 120 can be rotatable relative to the first plunger 103 and the second plunger 104.

As shown in FIGS. 4-5 and 8-9, the rotary arm module 102 can further include an arm (e.g., a chamfered arm) 117 extending radially outwardly from the flanged end 118 of the shaft 120 (i.e., radially outwardly, relative to the shaft axis S). As such, the arm 117 also resides outside (e.g., above) the second recess 124 of the second plunger 104 (as well as outside the tubular channel 169 of the first plunger 103). The arm 117 can be integrally formed with the shaft 120, as shown, or can be coupled thereto, to provide a moment arm for rotation of the shaft 120 about the shaft axis S and the axis A. The arm 117 and the latch 106 can be configured to inter-engage, such that the latch 106 can maintain the firing system 101 in its primed state and can be released to allow the stored energy of the stored energy device 109 to be released to cause the firing system 101 to fire, i.e., to change to its fired state.

As shown in FIGS. 3 and 6-9, the firing pin 110 can include a shaft (or cylindrical or tubular body) 113 having a shaft axis (e.g., a longitudinal axis) F (see FIGS. 6 and 7) configured to be oriented substantially in the axial direction (e.g., along the axis A) of the firing system 101 when the firing system 101 is assembled. The shaft 113 can be dimensioned to be received in the tubular channel 123 of the shaft 120 of the rotary arm module 102. In addition, in some embodiments, the firing pin 110 (and hence the projection 114) and the second plunger 104 can be configured to be fixedly coupled to one another, and particularly, to inhibit relative rotation between the firing pin 110 (and hence the projection 114) and the second plunger 104.

In some embodiments, the firing pin 110 and the second plunger 104 can include one or more inter-engaging features 116 (see FIGS. 3, 6-9 and 13) to accomplish this. As shown, in some embodiments, the inter-engaging features 116 can include one or more (two are shown by way of example) axial projections 126 on the firing pin 110 dimensioned to be received in one or more correspondingly shaped recesses 128 formed in the second plunger 104 (see FIGS. 3 and 13), and particularly, formed in a base of the second recess 124, to fixedly couple (e.g., rotationally fix) the firing pin 110 and the second plunger 104. By way of example only, the recess 128 shown in FIG. 13 is in the shape of a circle with two extending lobes. Such inter-engaging features 116 are shown by way of example only, however, it should be understood that other inter-engaging features can be used, such as one or more of a bolt, a rivet, an interference fit, a snap-fit, thermal and/or ultrasonic welding, an adhesive, a cohesive, a magnet, other suitable coupling means, or a combination thereof.

As described above, the projection 114 can be provided by the firing pin 110. In some embodiments, more than one projection 114 can be provided. For example, as shown, the firing pin 110 includes two projections 114, and particularly, two diametrically opposed projections 114, each dimensioned to be received in and movable along a guideway 121. As few as one projection 114 and as many as structurally possible and/or necessary for balanced, coordinated, and/or reliable operation of the firing system 101 can be employed. One projection 114 will be described in greater detail for simplicity, but it should be understood that the description of the projection 114 can be applied to as many projections 114 as employed.

As shown in FIGS. 6 and 7, the projection 114 can extend radially outwardly from the shaft 113 of the firing pin 110. In some embodiments, as further shown in FIGS. 6 and 7, the projection 114 can project or protrude from (and reside in) a flat, recessed area or region 115 formed in an outer surface of the shaft 113 of the firing pin 110. Furthermore, in some embodiments, the projection 114 can be chamfered on one or more of its edges, e.g., to facilitate relative movement with respect to the guideway 121. In addition, as shown in FIGS. 6 and 7, in some embodiments, the projection 114 can have a parallelogrammatic cross-sectional shape (e.g., taken along a direction oriented substantially perpendicularly with respect to the shaft axis F, or the axis A when the firing system 101 is assembled).

As further shown in FIGS. 7-9, in some embodiments, the projection 114 can be angled or tilted, such that the projection 114 is oriented at a non-zero and non-right angle with respect to the shaft axis F (and with respect to the axis A of the firing system 101 when assembled). When more than one projection 114 is employed, and particularly, when two opposing projections 114 are employed, the projections 114 can be inverted mirror images of one another (see FIG. 6), such that the firing pin 110 does not have mirror symmetry about a central longitudinal axis, but does have rotational symmetry (e.g., if rotated 180 degrees about its central longitudinal axis). As shown in FIGS. 8-9, the projection 114 can be configured to correspond with and to cam along the guideway 121.

The projection 114 can be dimensioned to be received in the guideway 121 in such a way that the projection 114 is movable in the guideway 121, and such that the projection 114 and the guideway 121 are movable with respect to one another between a first (e.g., primed) position (see FIG. 8) that corresponds to the first position of the second plunger 104 (and thus, the first plunger 103) and a second (e.g., fired) position (see FIG. 9) that corresponds to the second position of the second plunger 104 (and thus, the first plunger 103). As a result, the projection 114 is configured to cam along the guideway 121 when driven by, and in response to, the stored energy being released from the stored energy device 109 to cause the second plunger 104 to move (i.e., to translate in the axial direction) between its first position and its second position (i.e., as the projection 114 travels in the guideway 121, and particularly, as the projection 114 travels in the second portion 127 of the guideway 121). The guideway 121 can particularly be configured to allow rotary motion about the axis A to be transferred or converted to more axial (e.g., linear) motion (i.e., in a direction oriented along or parallel to the axis A, or at least more along or more parallel to the axis A).

In some embodiments, the rotary arm module 102, the firing pin 110, the convex circular spacer 105, and latch 106 can be formed of steel. In some embodiments, the preferred method of manufacturing such steel parts is by metal injection molding. In some embodiments, the first plunger 103, the second plunger 104, and the adapter 108 can be formed of a suitable plastic material. However, it will be obvious to one skilled in the art that other suitable materials and methods of manufacturing can be used.

As shown by a combination of FIGS. 3, 8-9, 15 and 18, when the firing system 101 is assembled, the base 49 of the canister 51 is received in the adapter 108, the upper portion of which is received in the first recess 111 of the second plunger 104; the firing pin 110 is located within the tubular channel 123 of the shaft 120 of the rotary arm module 102 (see FIG. 3); the projection 114 is positioned in the guideway 121; the shaft 120 of the rotary arm module 102, the firing pin 110, and the stored energy device 109 are received in the tubular channel 169 of the tubular projection 168 of the first plunger 103, all of which is received in the second recess 124 of the second plunger 104 (particularly, the stored energy device 109 of the illustrated embodiment is located between an outer surface of the shaft 120 of the rotary arm module 102 and an inner surface of the tubular channel 169 of the first plunger 103, as well as being located between the flanged end 118 of the shaft 120 and the base of the second recess 124 of the second plunger 104); the first seal 183 forms an air tight seal between an inner surface of the second recess 124 of the second plunger 104 and an outer surface of the tubular projection 168 of the first plunger 103; the second seal 184 forms an air tight seal between an inner surface of the outer sleeve portion 173 of the first plunger 103 and an outer surface of the outer sleeve portion 179 of the second plunger 104; the convex circular spacer 105 is positioned in the orifice 119 of the rotary arm module 102; and the inter-engaging features 116 of the firing pin 110 and the second plunger 104 are inter-engaged to fixedly couple, i.e., secure, the firing pin 110 (and the projection 114) to the second plunger 104.

Figure 15:
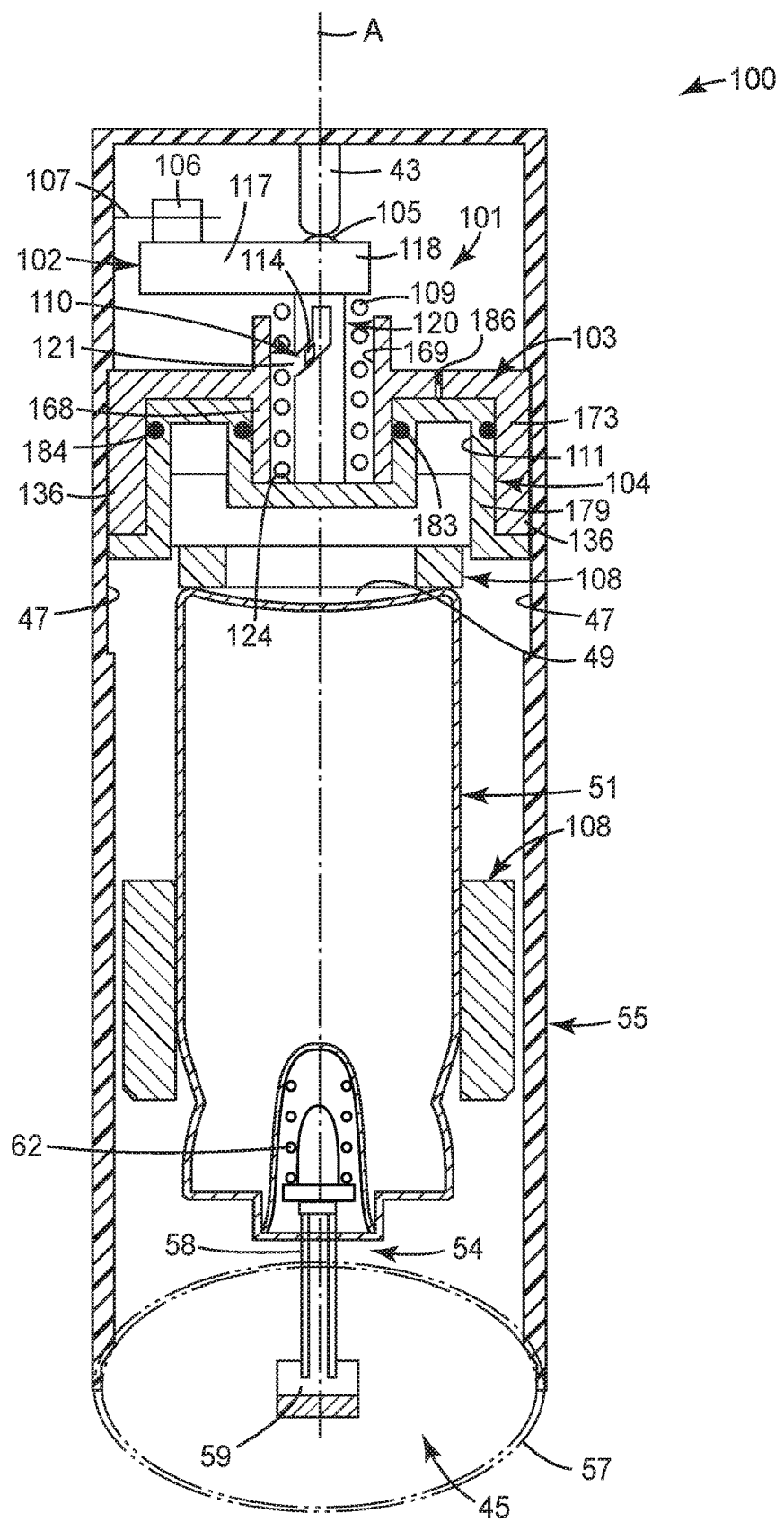
FIG. 15 is a schematic side cross-sectional view of the medicinal inhaler of FIG. 1, shown rotated 90 degrees about a longitudinal axis with respect to the side view shown in FIG. 1, the firing system being shown in its primed state.

The firing system 101 exists in three states: primed ('cocked'), fired and returned or reset. FIG. 15 illustrates the firing system 101 in its primed state in contact with the canister 51, with the stem portion 58 of the pMDI canister valve 54 seated in the stem socket 59, comprising the spray orifice 60, of the inhaler housing 55. As shown, the valve 54 can include an internal return biasing element 62 (e.g. a spring). In the primed state, the stored energy device 109, and particularly in embodiments in which the stored energy device 109 includes a biasing element, can be compressed between the rotary arm module 102 (e.g., the flanged end 118 thereof) and the second plunger 104 (e.g., the base of the second recess 124 thereof). Extending internally from the top of the inhaler housing 55 is a column 43 that has a convex end that is in contact over a small area with the convex circular spacer 105. The column 43 can provide a reaction surface for the stored energy device 109. That is, the force of the stored energy device 109, e.g., when including a biasing element, is resisted by the column 43, which presses against the convex circular spacer 105. The contact between the two convex surfaces is arranged to provide low friction, and hence minimal loss of energy due to friction, when the rotary arm module 102 rotates during actuation.

Figure 16:
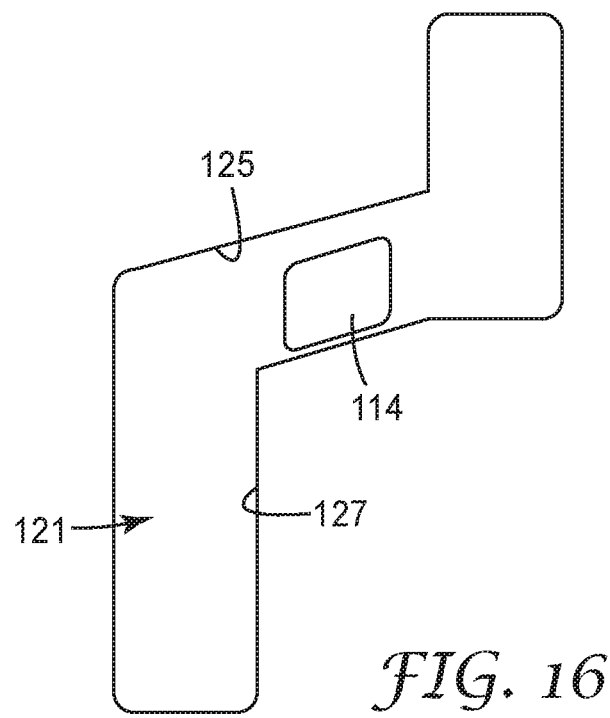
FIG. 16 is a schematic side 'un-rolled' flat view of the guideway of FIGS. 4, 5, and 8-9 and 15, the projection of FIGS. 3, 6-9 and 15 shown positioned in the guideway in a first position, when the firing system of FIGS. 1-3 and 15 is in its primed state.
Figure 17:
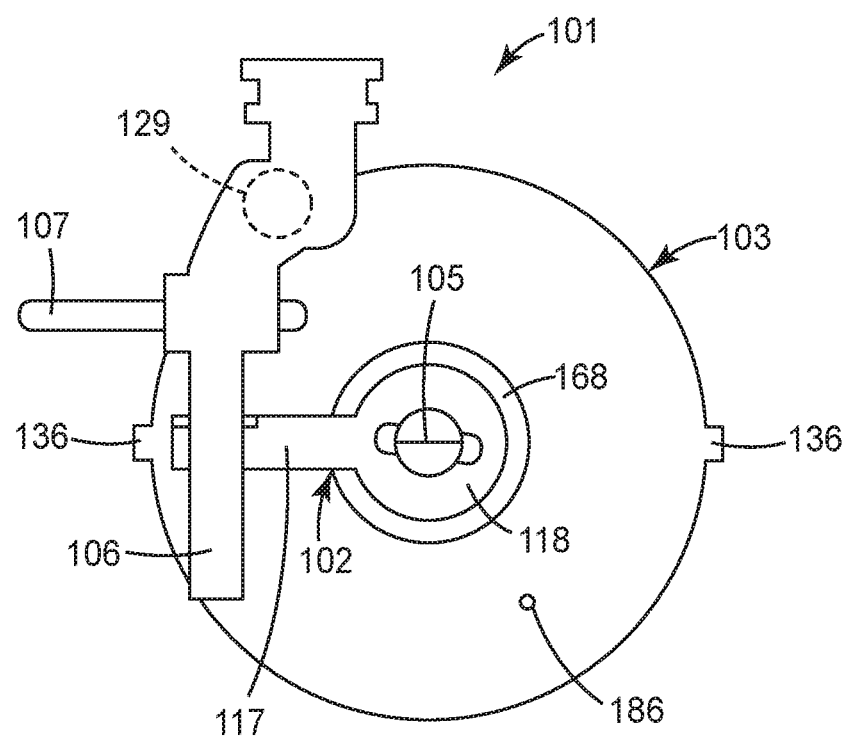
FIG. 17 is a top plan view of the firing system of FIGS. 1-3 and 15 when in its primed state.

In the primed state, the firing pin 110 is generally enveloped by the rotary arm module 102. FIGS. 8 and 16 illustrate the relative positions between the guideway 121 and the projection 114 in the primed state. By way of example only, FIG. 17 shows that the rotary arm module 102 is in a 9 o'clock position in the primed state, locked in place by the latch 106. As shown in FIGS. 1-3, 17 and 20, the firing system 101 can further include a return biasing element 129 located underneath the latch 106, which can be used to return the latch 106 to its first position, i.e., from its second position, as described in greater detail below. In some embodiments, the return biasing element 129 can include a spring, and particularly, a compression spring (e.g. with a compressed force of 2 N). The biasing element 129 can also ensure that the latch 106 remains engaged until it is desired to move the latch 106 from its first position to its second position (e.g., even if the firing system 101, or the inhaler 100, is shaken).

As mentioned earlier, the latch 106 can be movable between (i) a first (i.e., latched) position (see FIGS. 15 and 17) in which the latch 106 is coupled to at least one of the guideway 121 and the projection 114 (e.g., in the illustrated embodiment, the latch 106 is indirectly coupled to the guideway 121 via the arm 117 of the rotary arm module 102) to inhibit the guideway 121 and the projection 114 from moving relative to one another, the stored energy in the stored energy device 109 is held from being released, and the firing system 101 is in the primed state, and (ii) a second (i.e., unlatched) position (see FIGS. 18 and 20) in which the latch 106 is decoupled (i.e., released) from the guideway 121 and the projection 114 (e.g., in the illustrated embodiment, the latch 106 is released from the arm 117 of the rotary arm module 102), such that the guideway 121 and the projection 114 are free to move relative to one another, the stored energy of the stored energy device 109 is released, and the firing system 101 is free to change to the fired state. The stored energy device 109 can be configured and positioned, such that the stored energy is released in response to the latch 106 being moved from its first position to its second position.

That is, the latch 106 can be configured to: (i) maintain the firing system 101 in the primed state, wherein the guideway 121 and the projection 114 are stationary with respect to one another and the stored energy of the stored energy device 109 is not released, and (ii) release the firing system 101 from the primed state to allow the guideway 121 and the projection 114 to move relative to one another and to allow the stored energy of the stored energy device 109 to be released to drive the firing system 101 toward the fired state.

By way of example only, as shown in the illustrated embodiment, the latch 106 can be configured to be pivotally movable about a latch axis L (see FIG. 2A) between the first position and the second position. In some embodiments, the latch axis L can be oriented substantially perpendicularly with respect to the axis A of the firing system 101. The trigger 130 can be configured such that when the trigger 130 is actuated, as described in greater detail below, the trigger 130 can cause the latch 106 to move from its first position to its second position. For example, as shown in the illustrated embodiment, the trigger 130 can be actuated to cause the latch 106 to pivot on the pin 107 (e.g., about the latch axis L), thereby causing compression of the return biasing element 129.

In its second position, the latch 106 is no longer in contact with the rotary arm module 102, thus freeing the rotary arm module 102 to move, and also releasing the energy from the stored energy device 109. Particularly, in the illustrated embodiment, the stored energy device 109 is freed by release of the arm 117 of the rotary arm module 102. The release of the stored energy can thus begin to exert force on the rotary arm module 102. Release of the stored energy from the stored energy device 109 further drives the guideway 121 and the projection 114 to move relative to one another. As shown in FIG. 20, this is enabled by anti-clockwise rotation of the rotary arm module 102 through approximately 45° (as evident by comparing the position of the arm 117 in FIGS. 17 and 20).

Particularly, as shown in FIGS. 8 and 16, due to the configuration of the guideway 121 and the interaction between the guideway 121 and the projection 114, the guideway 121 and the projection 114 (e.g., when the projection 114 is received in the first portion 125 of the guideway 121), begin to rotate relative to one another. In embodiments in which the stored energy device 109 includes a spring, this allows the spring to uncompress. As shown in FIGS. 9 and 19, as the projection 114 and the guideway 121 continue to move relative to one another (i.e., from a primed position to a fired position), driven by the stored energy device 109, the projection 114 moves into the second portion 127 of the guideway 121, where the second helix angle is less than that of the first portion 125, such that the guideway 121 and the projection 114 can additionally or alternatively further translate relative to one another (e.g., in a direction oriented more axially with respect to the axis A).

Figure 18:
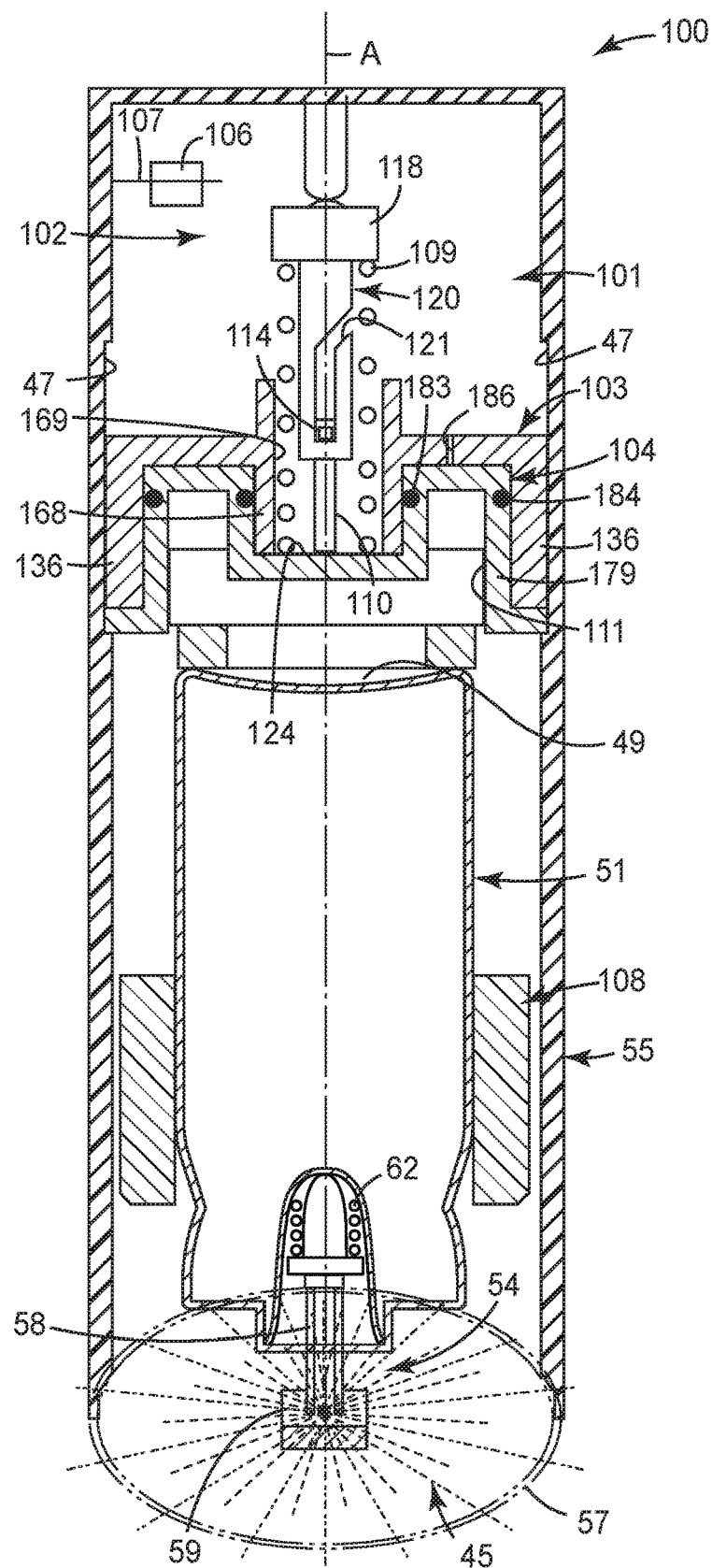
FIG. 18 is a schematic side cross-sectional view of the medicinal inhaler of FIGS. 1 and 15, shown in the same orientation as FIG. 15, the firing system being shown in its fired state.

The relative movement of the projection 114 and the guideway 121, shown by comparing FIGS. 8 and 16 with FIGS. 9 and 19, causes the second plunger 104 to move (e.g., axially) from its first position to its second position. Simultaneously, the first plunger 103 is forced to travel from its first position to its second position, as is the second plunger 104, as the mutual separation of the first plunger 103 and the second plunger 104 would lead to the creation of a significantly reduced air pressure (e.g., "vacuum") in the partially sealed evacuable chamber 185. As a result of the adapter 108 configuration and the coupling between the first plunger 103 and the adapter 108, movement of the first plunger 103 causes the adapter 108 and the canister 51 to move to their respective second positions, correlating with a dose release firing and a fired state of the inhaler 100, as shown in FIG. 18, where the metering valve 54 releases a dose. This is allowed as each projection 114 progresses in a guideway 121 from its first position (see FIG. 16) to its second position (see FIG. 19) with respect to the guideway 121. In the fired state shown in FIG. 18, the stored energy device 109 (e.g., shown in the form of a spring) is decompressed, the projection(s) 114 of the firing pin 110 have completed their full travel in the guideway(s) 121, and the valve return biasing element 62 (e.g., shown in the form of a spring) is compressed.

As described above, rotation of the second plunger 104 can be inhibited during firing due to the inter-engaging features between the second plunger 104 and the housing 55 of the inhaler 100 (e.g., due to the projections 177 of the second plunger 104 being seated in the recesses 47 of the housing 55), forcing the second plunger 104 to translate in the housing 55, i.e., to travel axially with respect to the axis A of the firing system 101. Similarly, rotation of the first plunger 103 can be inhibited during firing (e.g., due to the ribs 136).

The auto-reset function of the firing system 101 will now be described with reference to FIGS. 18, 21 and 22. As mentioned above, FIG. 18 shows the firing system 101 in a fired state, FIG. 21 shows the firing system 101 in a state intermediate between the fired state and a reset or returned state (i.e., during reset), and FIG. 22 shows the firing system 101 in a fully reset or returned state.

When the firing system 101 is in the primed state (described above and shown in FIG. 15), the stored energy is stored and not released from the stored energy device 109, the first plunger 103 and the second plunger 104 (e.g., the upper wall 187 of the first plunger 103 and the upper wall 188 of the second plunger 104) are separated by a first axial distance, which can be zero or greater. The plungers 103 and 104 move together to their second positions, as described above, such that when the firing system 101 is in the fired state (see FIG. 18), the stored energy is released from the stored energy device 109, and the first plunger 103 and the second plunger 104 (e.g., the upper wall 187 of the first plunger 103 and the upper wall 188 of the second plunger 104) are still separated by the first axial distance.

As mentioned above, in some embodiments, the canister 51 can be held in the fired position (see FIG. 18) for about 0.5 to 10 seconds to ensure that a full dose is dispensed. That is, the valve return biasing element 62 does not have sufficient force to overcome the stored energy device 109, nor to create a region of reduced air pressure in the evacuable chamber 185.

As shown in FIG. 21, resetting of the firing system 101 starts when there has been sufficient ingress of air through the vent 186, allowing the first plunger 103 to be pushed upwards away from the second plunger 104 under the force of the valve return biasing element 62 (e.g., from its compressed state) and against the differential air pressure formed by the separating motion of the first and second plungers 103 and 104. Due to the released stored energy from the stored energy device 109 (e.g., the bias of a spring) and the fact that the first plunger 103 is coupled to the adapter 108 and canister 51, while the second plunger 104 is not, the second plunger 104 remains in the fired state (i.e., in its second position) and does not move upwards with the first plunger 103 in response to the force provided by the valve return biasing element 62.

FIG. 22 shows the inhaler 100 with the firing system 101 in its reset or returned state, where the valve return biasing element 62 has completely returned to its rest state, and the evacuable chamber 185 has filled with air. As a result, both FIGS. 21 and 22 show the firing system 101 after firing (i.e., after valve actuation, i.e., after dose dispensing). As shown in FIGS. 21 and 22, the first plunger 103 and the second plunger 104 (e.g., the upper wall 187 of the first plunger 103 and the upper wall 188 of the second plunger 104) are separated by a second axial distance that is greater than the first axial distance of the primed and fired states. That is, the second plunger 104 remains in its second position, the stored energy of the stored energy device 109 remains released, but the first plunger 103 has separated from the second plunger 104 by a second axial distance that is greater than the first axial distance. That is, the second axial distance is nonzero and is greater than the first axial distance. Each of FIGS. 21 and 22 illustrate representative second axial distances between the first plunger 103 and the second plunger 104 (and accordingly, a third position of the first plunger 103), with FIG. 22 showing a fully reset state of the firing system 101 and a fully returned third position of the first plunger 103.

As a result, one dose release and reset process of the auto-reset dose release firing system 101 can be described as: (i) releasing stored energy from the stored energy device 109 to move the second plunger 104 from a first position to a second position; (ii) creating a reduced air pressure in the evacuable chamber 185 in response to moving the second plunger 104 from the first position to the second position; (iii) moving the first plunger 103 from a first position to a second position with the second plunger 104 as a result of the reduced air pressure created in the evacuable chamber 185; and (iv) moving the first plunger 103 from the second position to a third position in response to air entering the evacuable chamber 185 via the vent 186.

The process can further include (v) actuating the dose release valve 54 of the canister 51 to open, i.e., in response to moving the first plunger 103 from the first position to the second position; and (vi) closing the dose release valve of the canister 51 in response to moving the first plunger 103 from the second position to the third position. As mentioned above, the time between opening and closing the dose release valve 54 can be at least about 0.5 seconds, and in some embodiments, can be no greater than about 10 seconds.

Return of the firing system 101 to its primed state can be achieved by a priming (or "re-priming" or "cocking") mechanism 160 that can be coupled to the inhaler 100 and/or the firing system 101, as shown in FIG. 22. Referring to FIG. 22, in some embodiments, priming or cocking can be achieved via one or more cams 162 (e.g., 'egg' shaped cams or eccentric cams) and a handle (or "lever," or "cocking lever") 164. As shown in FIG. 22, after firing and firing reset the second plunger 104 remains in its second position and is coupled to (e.g., in contact with) the cam(s) 162. Application of a pulling force (e.g., an upward pulling force) on the handle 164 results in rotation of the cam(s) 162. The rotation of the cam(s) 162 therefore drives the second plunger 104 upwards from its second position to its first position. In the illustrated embodiment, this motion applies a force in a direction opposite to the spring force of the stored energy device 109, developing a load, or stored energy, in the stored energy device 109.

Movement of the second plunger 104 from its second position to its first position further causes each projection 114 to travel back up the corresponding guideway 121 (e.g., compressing the spring of the stored energy device 109, when employed), and further causes the rotary arm module 102 to return to its 9-o'clock position shown in FIG. 17. When the triggering force (e.g., by the trigger 130) is no longer being applied to the latch 106, the return biasing element 129 applies a small force to the latch 106, causing the latch 106 to move from its second position to its first position, thus ensuring that it returns to full latching engagement with the rotary arm module 102 (e.g., with the arm 117 thereof). The user can then return the handle 164 to its starting position, which rotates the cam(s) 162 in the opposite direction, causing the cam(s) 162 to become decoupled from the second plunger 104. The priming mechanism 160 is shown by way of example as including two cams 162, and particularly, two diametrically opposed cams 162, but this need not be the case. As few as one cam 162 and as many as structurally necessary can be employed to prime the firing system 101.

As a result, one re-priming process of the firing system 101 can include moving the second plunger 104 to the first position (i.e., from the second position) and causing energy to be stored in the stored energy device 109.

The above described priming mechanism 160 is shown and illustrated in FIG. 22 by way of example only. However, it should be understood that other priming mechanisms can be employed to return all of the elements of the firing system 101 to their respective first positions and to return the firing system 101 to a starting or primed state. For example, in some embodiments, arrangements other than the handle 164 (e.g., a pivoting mouthpiece cover) can be used to re-prime the firing system 101.

The configuration of the firing pin 110 and rotary arm module 102 providing the projection 114 and the guideway 121, respectively, can offer benefits of compactness and manufacturing ease. However, it will be obvious to one skilled in the art that other arrangements are possible. For example, as mentioned above, in some embodiments, the guideway 121 may not be formed through the thickness of the wall 122 of the shaft 120. In some embodiments, the wall thickness of the shaft 120 can be greater, thereby allowing the one or more guideways 121 to be formed entirely within the thickness of the wall 122 of the shaft 120, creating an unbroken outer surface to the shaft 120. Such an embodiment can confer additional strength to the rotary arm module 102, but generally requires a more sophisticated manufacturing method (e.g., injection moulding using collapsing cores, additive manufacturing technology, other suitable methods, or a combination thereof).

In some embodiments, the one or more guideways 121 can include a larger helical portion, where one or more guideways 121 include at least one 360 degree portion about the circumference of the shaft 120. In such embodiments, a rotating molding tool core can be used to injection mold such a part.

In some embodiments, one or more projections 114 can be located on the rotary arm module 102 (e.g., extending outwardly from an outer surface of the shaft 120 thereof), which can be located within a hollow firing pin 110 (i.e., the reverse of the illustrated embodiment). Such projection(s) 114 could extend through a wall thickness of the firing pin shaft 113, or they could be shorter and engage in a guideway 121 formed within the inner part of the firing pin 110 (e.g., within the inner portion of a thick hollow firing pin shaft wall), allowing the outside of the firing pin shaft wall to be unbroken and continuous, e.g., for reasons of strength.

The number, configuration, and sizes of the projections 114 and guideways 121 of the firing systems 101 of the present disclosure may be chosen to suit a particular application, these details being capable of determination by one skilled in the art. Furthermore, in some embodiments, the angle of the projection(s) 114 (e.g., with respect to the axis A) and shape/angles of the guideway(s) 121 may be chosen to customize a firing system for a particular application, e.g., for pMDI canister valves with differing properties, if required.

As described earlier, the trigger 130 can be used to apply a triggering force to the latch 106 to move the latch 106 from its first position to its second position to allow release of the firing system 101 from its primed state. That is, the trigger 130 can be operatively coupled to the latch 106 and configured to change between a first state and a second state to move the latch between the first position and the second position, respectively (i.e., to allow the firing mechanism 101 to be fired). In some embodiments, the trigger 130 can be breath-actuated. In some embodiments, the trigger 130 can be configured to change between its first state and its second state in response to non-mechanical energy (e.g., an electrical signal); and in some embodiments, the trigger 130 can be configured to change between its first state and its second state in response to mechanical energy.

Various embodiments of triggers of the present disclosure will now be described in greater detail with respect to FIGS. 1 and 23-26. For simplicity, the remainder of the firing system components of exemplary FIGS. 23-26 are the same as those of the firing system 101 described above.

As shown in FIG. 1, the inhaler 100 includes a trigger 130 according to one embodiment of the present disclosure. By way of example only, the trigger 130 includes a shape memory material, e.g., a shape memory alloy (SMA) wire 131, coupled to the latch 106 and positioned to provide force to the latch 106 to move the latch 106 from its first position to its second position. Particularly, a first portion of the SMA wire 131 can be coupled to (e.g., looped over and/or tied to) an end of the latch 106 that is on the opposite side of the pin 107 from an end of the latch 106 that is configured to retain the rotary arm module 102 (e.g., the arm 117 thereof), and a second portion of the SMA wire 131 can be secured in a fixed location in the housing 55, e.g., by one or more crimps 133. The crimps 133 can be coupled to, or in communication with, the controller 151. The SMA wire 127 can be powered using an appropriate power source (not shown), such as a cell or a battery of cells.

Actuation, or firing, of the firing system 101 can occur when the appropriate signal is received by the controller 151, which can be in the form of an electrical signal from a user-operated switch (not shown) on the inhaler housing 55, e.g., in a form of a "press and breath" arrangement, or in the form of one or more signals from one or more sensing elements present in the inhaler 100, such as those of the inspiratory air flow detection system 150, i.e., in a breath-actuated arrangement.

Upon receiving the appropriate signal(s), the controller 151 sends an electrical current, or other form of non-mechanical energy, to the SMA wire 131 (e.g., for approximately 0.2 s), causing the SMA wire 131 to heat up due to its resistance and therefore causing it to contract as a result of the solid state microstructural transformation that such materials exhibit when appropriately heated. In some embodiments, the transformation temperature of the SMA wire 131 can be about 90° C., and when actuated, the controller 151 can be configured to create an electrical current to heat the SMA wire 131 to a temperature of around 90° C. Contraction of the SMA wire 131 results in a pulling force being applied to the latch 106 to move the latch 106 from its first position to its second position, and particularly, causing it to pivot on its pin 107 to release the rotary arm module 102 (e.g., the arm 117 thereof), allowing the stored energy device 109 to be released to drive the second plunger 104 (and hence, the first plunger 103) to move from its first position to its second position to cause valve actuation (i.e., actuation of the valve 54 to dispense a dose of medicament from the spray orifice 60).

Upon cessation of the heating current from the controller 151, loss of heat from the SMA wire 131 allows it to return to its original state, the SMA wire 131 thereby lengthening again (e.g., under the action of the return biasing element 129). In some embodiments, cooling of the SMA wire 131 can take about 1 s to reach room temperature (e.g., 20-25° C.). After firing, the firing system 101 can be re-primed as described previously.

In some embodiments, the SMA wire 131 can be a nickel-titanium alloy comprising 50% nickel and 50% titanium, the diameter of the SMA wire 131 can be about 75 μm and it can have a length of about 60 mm. Using an SMA wire 131 with the described properties and a 1.5 V lithium ion cell, the contraction of the SMA wire 131 can take about 0.2 s, and the SMA wire 131 can transition to its second, contracted, state between 70-90° C. After approximately 0.2 s the controller 151 can be programmed to stop the electrical current, allowing the SMA wire 131 to return to its first state. In some embodiments, multiple loops or lengths of the SMA wire 131 can be employed. In some embodiments, an SMA comprising a different compositional makeup (e.g., different percentages of nickel and titanium, and/or comprising an alloy of different metals) can be employed. In addition, in some embodiments, different means for coupling the SMA wire 131 to the controller 151 can be employed, and the one or more crimps 133 are shown by way of example only.

Additional exemplary embodiments of triggers of the present disclosure will now be described with respect to FIGS. 23-26, wherein like numerals reference like elements. Reference is made to the description above accompanying FIG. 1 for a more complete description of the features and elements (and alternatives to such features and elements) of the inhaler 100 and the firing system 101. The dedicated air flow path 146, the flow governor 140, and the inspiratory air flow detection system 150 have been removed from FIGS. 23-26 for simplicity and clarity. However, it should be understood that any of the features described above with respect to FIGS. 1-22 can be applied to the embodiments of FIGS. 23-26, and vice versa. Alternatively, an air inlet for the inhaler can be formed in or provided by another region of the inhaler shown in FIGS. 23-26.

Figure 23:
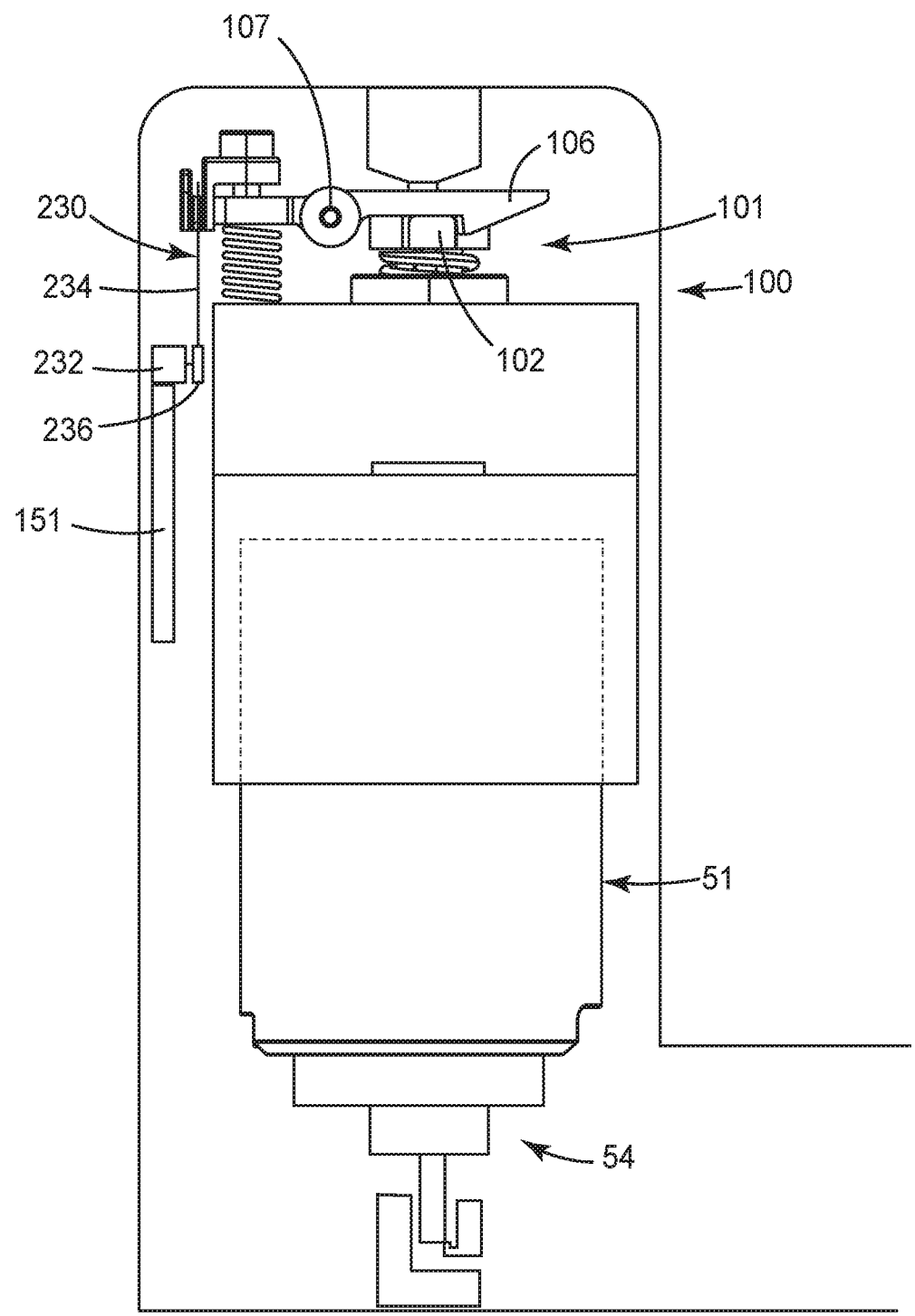
FIG. 23 is a cutaway side elevational view of the medicinal inhaler of FIG. 1, with portions removed for clarity, comprising a trigger according to another embodiment of the present disclosure that includes a digital motor.

FIG. 23 illustrates a trigger 230 according to another embodiment of the present disclosure, the trigger 230 being shown in combination with the firing system 101 and other elements of the inhaler 100 of FIGS. 1-22. The trigger 230 includes a digital motor 232 to provide force to the latch 106 to move the latch 106 from its first position to its second position. The trigger 230 of FIG. 23 further includes a length of filament 234 (e.g., nylon or other suitable thread-like material) positioned to couple the latch 106 to a spool 236 attached to the digital motor 232 in communication with the controller 151. The digital motor and the controller 151 can be powered using an appropriate power source (not shown), such as a battery.

Actuation of the firing system occurs when the appropriate signal(s) is/are received by the controller 151, as described previously. Upon receiving the appropriate signal (s), the controller 151 sends an electrical current to the digital motor 232 causing the filament 234 to be taken up by the spool 236 (i.e., wound around the spool 236). This results in shortening of the extended length of the filament 234, which causes the end of the latch 106 opposite the end retaining the rotary arm module 102 to pivot on its pin 107 and release the rotary arm module 102, thereby releasing the firing system 101 to fire, allowing actuation of the metering dose valve 54 of the pMDI canister 51. As will be appreciated by a person of ordinary skill in the art, the controller 151 can cause the current to be switched off (i.e., after firing), disabling the trigger and allowing the system 101 to be reset and/or re-primed. The firing system 101 can be re-primed as described above.

Figure 24:
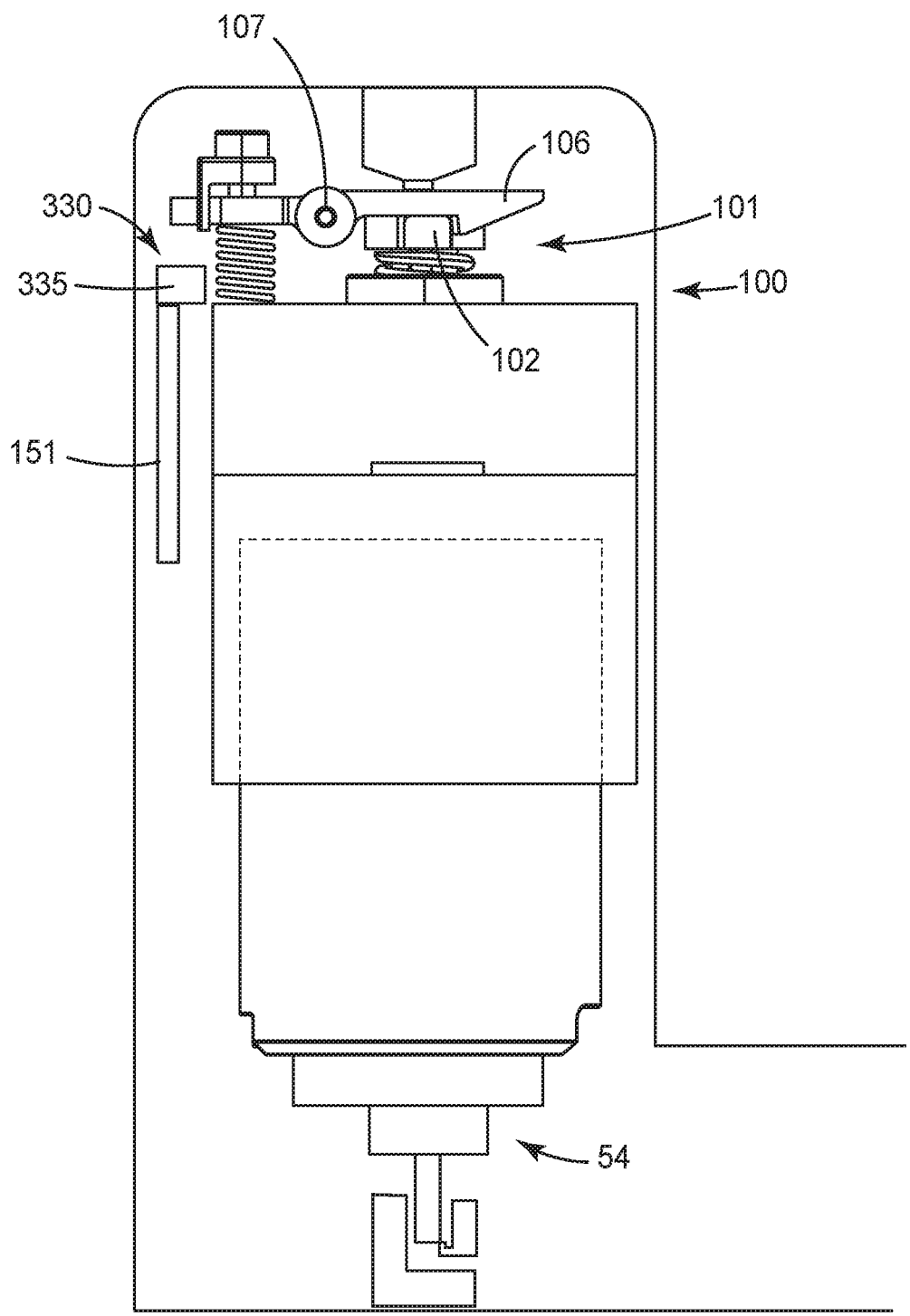
FIG. 24 is a cutaway side elevational view of the medicinal inhaler of FIG. 1, with portions removed for clarity, comprising a trigger according to a further embodiment of the present disclosure that includes an electromagnet.

FIG. 24 illustrates a trigger 330 according to another embodiment of the present disclosure, the trigger 330 being shown in combination with the firing system 101 and other elements of the inhaler 100 of FIGS. 1-22. The trigger 330 includes an electromagnet 335 to provide force to the latch 106 to move the latch 106 from its first position to its second position. The electromagnet 335 is in communication with (i.e., is electrically connected to) the controller 151. The electromagnet 335 and the controller 151 can be powered using an appropriate power source (not shown), such as a battery.

Actuation of the firing system occurs when the appropriate signal(s) is/are received by the controller 151, as described previously. Upon receiving the appropriate signal (s), the controller 151 sends an electrical current to the electromagnet 335. The resultant magnetic force can be configured to attract the end of the latch 106 opposite the end retaining the rotary arm module 102 to cause the latch 106 to pivot on its pin 107 and release the rotary arm module 102, thereby releasing the firing system 101 to fire, allowing actuation of the metering dose valve of the pMDI canister 51. As will be appreciated by a person of ordinary skill in the art, the controller 151 can cause the current to be switched off (i.e., after firing), disabling the trigger and allowing the system 101 to be reset and/or re-primed. The firing system 101 can be re-primed as described above.

Figure 25:
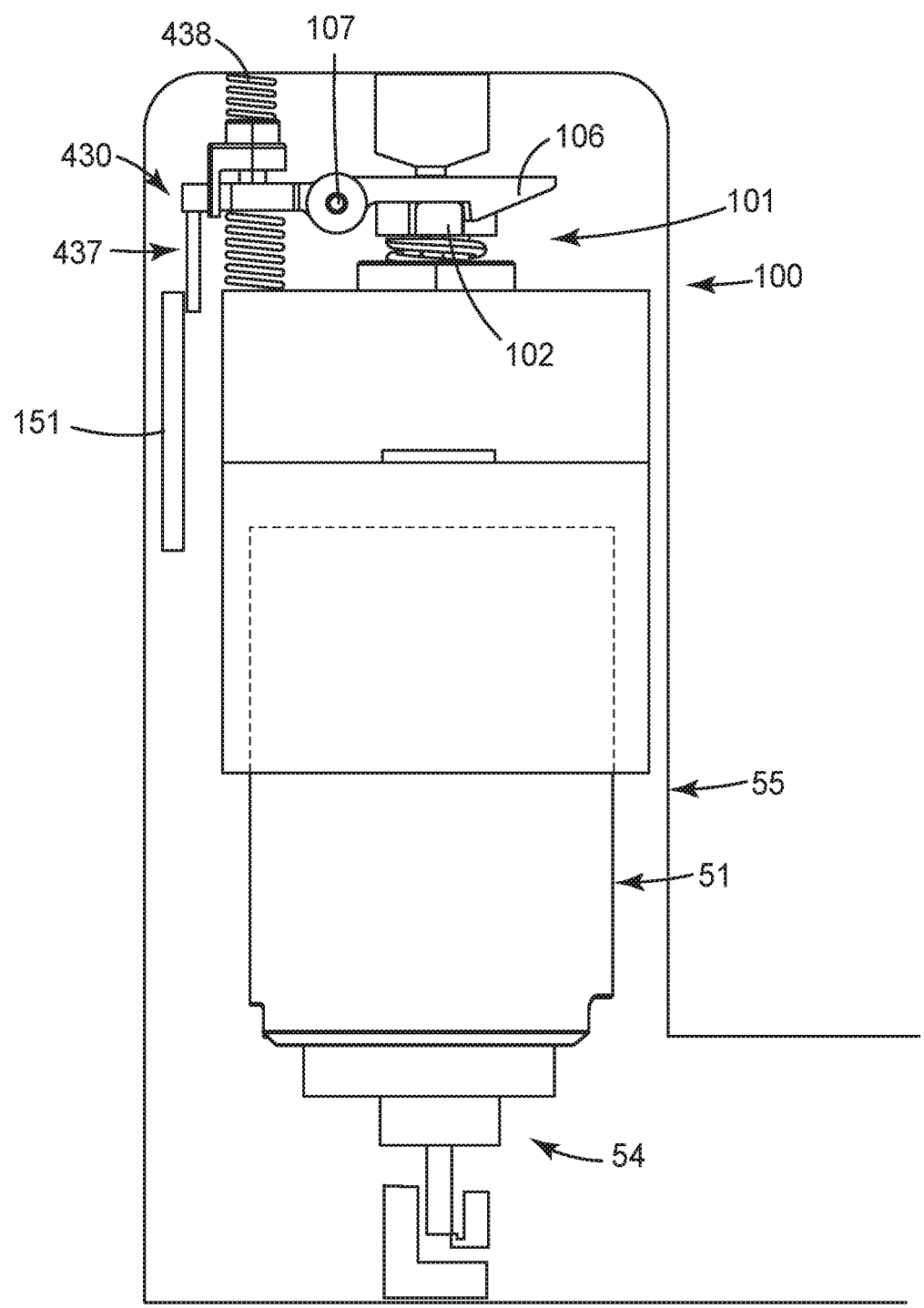
FIG. 25 is a cutaway side elevational view of the medicinal inhaler of FIG. 1, with portions removed for clarity, comprising a trigger according to yet another embodiment of the present disclosure that includes a solenoid.

FIG. 25 illustrates a trigger 430 according to another embodiment of the present disclosure, the trigger 430 being shown in combination with the firing system 101 and other elements of the inhaler 100 of FIGS. 1-22. The trigger 430 includes a solenoid 437 to provide force to the latch 106 to move the latch 106 from its first position to its second position. The solenoid 437 is in communication with (i.e., is electrically connected to) the controller 151. The solenoid 437 and/or the controller 151 can be powered using an appropriate power source (not shown), such as a battery. The trigger 430 can further include a biasing element 438 (e.g., a spring), under compression, located, for example, between the latch 106 and a portion of the housing 55. The biasing element 438 can provide an opposing biasing force to the solenoid 437. That is, the solenoid 437 and the biasing element 438 can oppose one another, such that the solenoid 437 opposes the forces exerted by the biasing element 438.

Actuation of the firing system occurs when the appropriate signal(s) is/are received by the controller 151, as described previously. Upon receiving the appropriate signal (s), the controller 151 sends an electrical current to the solenoid 437, causing it to actuate. This allows the biasing element 438 to exert its force on the end of the latch 106 opposite the end retaining the rotary arm module 102 to cause the latch 106 to pivot on its pin 107 and release the rotary arm module 102, thereby releasing the firing system 101 to fire, allowing actuation of the metering dose valve of the pMDI canister 51. The firing system 101 can be re-primed as described above.

A further advantage with using an electronic mechanism to release the latch 106 of the firing system 101 is that the controller 151 can be designed to communicate with a memory device incorporated into the inhaler 100. The electronic circuitry involved can be configured to allow each firing system triggering event to be counted and recorded, and can be used to also provide a dose count, e.g., for display to the patient on the inhaler 100 of the theoretical number of doses thus still remaining.

In embodiments in which one or more pressure sensors (see, e.g., the pressure sensors 152a and 152b of FIG. 1) are used to detect and measure the patient's inspiratory efforts, not only can the calculated air flow rate data be used to trigger dose release firing via a firing system of the present disclosure (e.g., the firing system 101), but incorporation of an appropriate electronic memory device can also allow the capture, storage and/or retrieval of the patient's inhalation profile (flow rates, pressure drops, etc.) corresponding to each time the inhaler was used. This information can be displayed for the user to see or a means to transmit these data, via a cable or using wireless technology, to a secondary device (e.g., to a computer or a 'smart' phone), can be included for future data retrieval to allow analysis and interpretation of the frequency and times of doses. These data could be made available to the patient's physician or others, in order to allow them to monitor the patient's ability to use the inhaler successfully and to allow appropriate and timely health care advice to be provided based on analysis and interpretation of the retrieved information.

Figure 26:
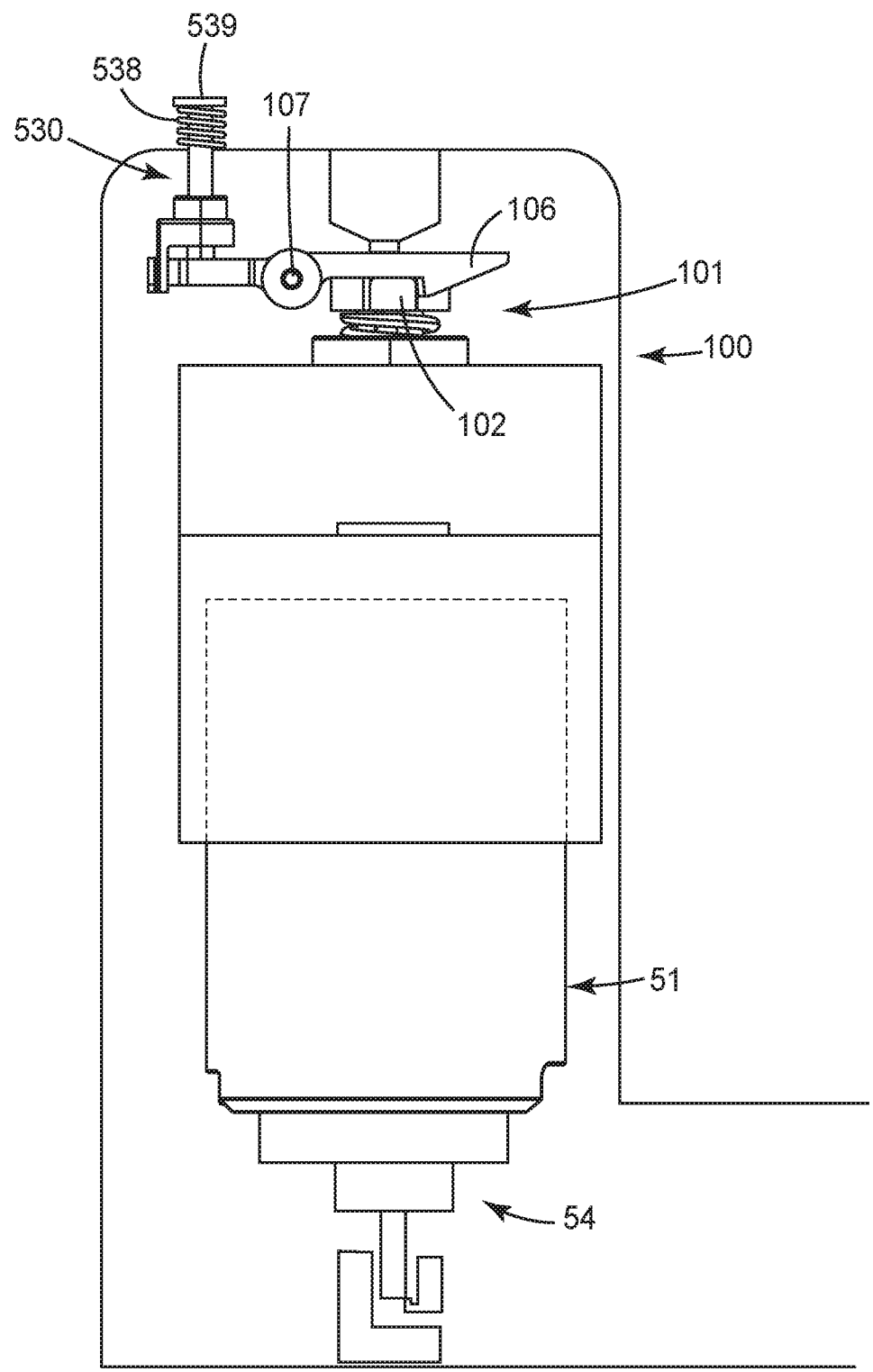
FIG. 26 is a cutaway side elevational view of the medicinal inhaler of FIG. 1, with portions removed for clarity, comprising a trigger according to yet a further embodiment of the present disclosure that includes a mechanical actuator.

FIG. 26 illustrates a trigger 530 according to another embodiment of the present disclosure, the trigger 530 being shown in combination with the firing system 101 and other elements of the inhaler 100 of FIGS. 1-22. The trigger 530 includes a mechanical actuator 539 configured to cooperate with the latch 106 to provide force to the latch 106 to move the latch 106 from its first position to its second position. As shown in FIG. 26, in some embodiments, the mechanical actuator 539 can be in the form of a push button, and can further include a return biasing element 538 shown in the form of a spring.

When mechanical energy is applied to the mechanical actuator 539 (e.g., when the push button is pressed), the biasing element 538 is compressed and the mechanical force from the mechanical actuator 539 is applied to the latch 106, and particularly to the end of the latch 106 opposite the end retaining the rotary arm module 102, to cause the latch 106 to pivot on its pin 107 and release the rotary arm module 102, thereby releasing the firing system 101 to fire, allowing actuation of the metering dose valve of the pMDI canister 51. The firing system 101 can be re-primed as described above.

In some embodiments, the mechanical actuator 539 can be incorporated on its own to release the latch 106, or with an electronic mechanism such as one of those described above. Such an embodiment can provide a 'fail safe' arrangement for instances in which the electronic system fails.

Additional details regarding firing systems that can be employed in combination with the auto-reset functions of the present disclosure, in inhalers of the present disclosure, can be found in PCT Publication Nos. WO2017/112476 and WO2017/112400, each of which is incorporated herein by reference in its entirety. The specific firing system 101 (e.g., comprising the firing pin 110, the rotary arm module 102, the stored energy device 109, and the latch 106, etc.) is shown and described herein by way of example only, and it should be understood that other firing systems can be employed in combination with the dual-plunger auto-reset mechanisms of the present disclosure, in inhalers of the present disclosure, without departing from the spirit and scope of the present disclosure.

Each embodiment shown in the figures is illustrated as a separate embodiment for clarity in illustrating a variety of features of the firing systems and inhalers of the present disclosure. However, it should be understood that any combination of elements and features of any of the embodiments illustrated in the figures and described herein can be employed in the firing systems and inhalers of the present disclosure.

The following embodiments are intended to be illustrative of the present disclosure and not limiting.

Embodiments

1. An auto-reset dose release firing system for use in a medicinal inhaler, the system comprising
an axis that defines an axial direction that extends along or substantially parallel to the axis;
a stored energy device, wherein the firing system is in a primed state when stored energy of the stored energy device is not released, and wherein the firing system is in a fired state when the stored energy is released;
a first plunger movable in the axial direction between a first position, a second position, and a third position, wherein the first plunger is configured to be operatively coupled to a medicament canister of the medicinal inhaler to actuate a dose release valve of the medicament canister when the first plunger is in the second position; and
a second plunger movable in the axial direction between a first position and a second position, wherein the second plunger is not configured to be coupled to the medicament canister, wherein the second plunger is positioned to be driven by the stored energy device of the firing system from its first position to its second position when the stored energy is released, wherein the first plunger and the second plunger are movable with respect to one another in the axial direction and are shaped to define an evacuable chamber therebetween;
wherein the first plunger and the second plunger are separated by a first axial distance when the firing system is in the primed state and the first plunger and the second plunger are each in the first position, wherein the first axial distance is at least zero;
wherein the first plunger and second plunger are separated by the first axial distance when the firing system is in the fired state and the first plunger and the second plunger are each in the second position; and
wherein the first plunger and the second plunger are separated by a second axial distance when the firing system is in a reset state, the second plunger is in the second position, and the first plunger is in the third position, wherein the second axial distance is nonzero and is greater than the first axial distance.

2. The system of embodiment 1, further comprising a seal positioned between the first plunger and the second plunger.

3. The system of embodiment 1 or 2, wherein the evacuable chamber includes a vent dimensioned to provide a reduced air pressure in the evacuable chamber when the first plunger and the second plunger are moved from the first position to the second position and further dimensioned to allow air ingress at a desired rate to move the first plunger from its second position to its third position.

4. The system of any of embodiments 1-3, wherein at least one of the first plunger and the second plunger is dimensioned to receive at least a portion of the second plunger and the first plunger, respectively.

5. The system of any of embodiments 1-4, wherein the first plunger and the second plunger include inter-engaging structures.

6. The system of any of embodiments 1-5, wherein the first plunger includes an outer sleeve portion dimensioned to receive at least a portion of the second plunger, such that the first plunger forms an outer plunger and the second plunger forms an inner plunger.

7. The system of any of embodiments 1-6, wherein the first plunger includes an annular recess dimensioned to receive an annular projection of the second plunger.

8. The system of embodiment 7, wherein the annular projection extends axially away from a medicament canister of the medicinal inhaler.

9. The system of any of embodiments 1-8, wherein the second plunger includes a central tubular recess dimensioned to receive a central tubular projection of the first plunger.

10. The system of embodiment 9, wherein the tubular projection extends axially toward a medicament canister of the medicinal inhaler.

11. The system of any of embodiments 1-10, wherein the second plunger includes an annular recess dimensioned to receive at least a portion of an adapter configured to house at least a portion of a medicament canister of the medicinal inhaler.

12. The system of any of embodiments 1-11, wherein the first plunger is configured to be operatively coupled to a medicament canister of the medicinal inhaler via an adapter configured to house at least a portion of the medicament canister.

13. The system of any of embodiments 1-12, wherein the first plunger and the second plunger are rotationally fixed with respect to the axis.

14. The system of any of embodiments 1-13, further comprising:
  a guideway, wherein at least a portion of the guideway has a helical shape, the guideway having a first portion having a first helix angle with respect to the axis that is greater than zero, and a second portion having a second helix angle with respect to the axis, wherein the second helix angle is less than the first helix angle; and
  a projection dimensioned to be received in the guideway, the projection being movable in the guideway between a first position corresponding to the first position of the first plunger and a second position corresponding to the second position of the second plunger, such that the projection is configured to be cammed along the guideway when the stored energy device drives the second plunger to move from the first position to the second position;
  wherein the guideway or the projection is fixedly coupled to the second plunger.

15. The system of any of embodiments 1-14, wherein the stored energy device includes a biasing element.

16. The system of any of embodiments 1-15, wherein the stored energy device is configured to provide at least 40 N of force when the stored energy is released.

17. The system of any of embodiments 1-16, wherein the firing system is breath-actuated.

18. The system of any of embodiments 1-17, wherein the first plunger and the second plunger are coaxial.

19. A medicinal inhaler comprising the auto-reset dose release firing system of any of the preceding embodiments (e.g., positioned in a housing), wherein the medicinal inhaler is a pressurized metered dose inhaler (pMDI).

20. A medicinal inhaler comprising the auto-reset dose release firing system of any of the preceding embodiments (e.g., positioned in a housing), wherein the medicinal inhaler is at least one of a breath-actuated inhaler, a pressurized metered dose inhaler (pMDI), a dry powder inhaler (DPI), a nebulizer, and a combination thereof.

21. A medicinal inhaler comprising:
  a housing;
  a canister comprising a medicament positioned in the housing; and
  the auto-reset dose release firing system of any of the preceding embodiments positioned in the housing, with the first plunger operatively coupled to the canister.

22. A method for releasing a dose of medicament from a medicinal inhaler:
  providing a stored energy device, wherein the firing system is in a primed state when stored energy of the stored energy device is not released, and wherein the firing system is in a fired state when the stored energy is released;
  providing a first plunger movable along the axis between a first position, a second position, and a third position, wherein the first plunger is configured to be operatively coupled to a medicament canister of the medicinal inhaler to actuate a dose release valve of the medicament canister when the first plunger is in the second position; and
  providing a second plunger movable along the axis between a first position and a second position, wherein the second plunger is not configured to be coupled to the medicament canister, wherein the second plunger is positioned to be driven by the stored energy device of the firing system from its first position to its second position when the stored energy is released, wherein the first plunger and the second plunger are movable with respect to one another in the axial direction and are shaped to define an evacuable chamber therebetween;
  releasing stored energy from the stored energy device to move the second plunger from the first position to the second position;
  creating a reduced air pressure in the evacuable chamber in response to moving the second plunger from the first position to the second position;
  moving the first plunger from the first position to the second position with the second plunger as a result of the reduced air pressure created in the evacuable chamber; and
  moving the first plunger from the second position to the third position in response to air entering the evacuable chamber via a vent.

23. The method of embodiment 22, further comprising re-priming the system by moving the second plunger to the first position and causing energy to be stored in the stored energy device.

24. The method of embodiment 22 or 23, further comprising:
  actuating a dose release valve of a medicament canister to open in response to moving the first plunger from the first position to the second position;
  closing the dose release valve of the medicament canister in response to moving the first plunger from the second position to the third position.

25. The method of embodiment 24, wherein the time between opening and closing the dose release valve is at least about 0.5 seconds.

26. The method of embodiment 24 or 25, wherein the time between opening and closing the dose release valve is no greater than about 10 seconds.

27. The method of any of embodiments 22-26, wherein:
  the first plunger and the second plunger are separated by a first axial distance when the firing system is in the primed state and the first plunger and the second plunger are each in the first position, wherein the first axial distance is at least zero;
  the first plunger and second plunger are separated by the first axial distance when the firing system is in the fired state and the first plunger and the second plunger are each in the second position; and
  the first plunger and the second plunger are separated by a second axial distance when the firing system is in the fired state, the second plunger is in the second position, and the first plunger is in the third position, wherein the second axial distance is nonzero and is greater than the first axial distance.

Some aspects of the present disclosure provide a medicinal inhaler comprising an actuation triggering system with a valve reset mechanism;
  the medicinal inhaler comprising a system to generate an electrical impulse signal in response to a detected inspiratory air flow through the inhaler;

the actuation triggering system being operable to release a supply of stored energy to operate an aerosol dose dispenser to dispense a dose of aerosolised medicament; and the valve reset mechanism allowing automatic valve reset after a dose of medicament has been dispensed; wherein, in some embodiments, the triggering system can include a shape memory alloy wire that is heated by an electrical impulse signal, the heating causing the wire to shorten and to release a latch, release of the latch causing the supply of stored energy to operate the aerosol dose dispenser.

In some embodiments, the automatic valve reset mechanism comprises a first and second plunger that are positioned in close juxtaposition at the start of the aerosol dose dispenser operation and which separate as air leaks into a region of reduced pressure between them over a period of time, thereby allowing the aerosol dose dispenser to return to its starting position.

In some embodiments, the automatic valve reset mechanism allows the aerosol dose dispenser to return to its starting or rest position after a predetermined time delay after dose release. In some embodiments, the medicinal inhaler can further include a flow governor with the ability to change its geometry and resistance to air flow as a function of the pressure drop it experiences.

It is to be understood that the invention is not limited in its application to the details of construction and the arrangement of components set forth in the above description or illustrated in the accompanying drawings. The invention is capable of other embodiments and of being practiced or of being carried out in various ways. Also, it is to be understood that the phraseology and terminology used herein is for the purpose of description and should not be regarded as limiting. It is to be further understood that other embodiments may be utilized, and structural or logical changes may be made without departing from the scope of the present disclosure.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. An auto-reset dose release firing system for use in a medicinal inhaler, the system comprising
   an axis that defines an axial direction that extends along or substantially parallel to the axis;
   a stored energy device, wherein the firing system is in a primed state when stored energy of the stored energy device is not released, and wherein the firing system is in a fired state when the stored energy is released;
   a first plunger movable in the axial direction between a first position, a second position, and a third position, wherein the first plunger is configured to be operatively coupled to a medicament canister of the medicinal inhaler to actuate a dose release valve of the medicament canister when the first plunger is in the second position; and
   a second plunger movable in the axial direction between a first position and a second position, wherein the second plunger is not configured to be coupled to the medicament canister, wherein the second plunger is positioned to be driven by the stored energy device of the firing system from its first position to its second position when the stored energy is released, wherein the first plunger and the second plunger are movable with respect to one another in the axial direction and are shaped to define an evacuable chamber therebetween;
   wherein the first plunger and the second plunger are separated by a first axial distance when the firing system is in the primed state and the first plunger and the second plunger are each in the first position, wherein the first axial distance is at least zero;
   wherein the first plunger and second plunger are separated by the first axial distance when the firing system is in the fired state and the first plunger and the second plunger are each in the second position; and
   wherein the first plunger and the second plunger are separated by a second axial distance when the firing system is in a reset state, the second plunger is in the second position, and the first plunger is in the third position, wherein the second axial distance is nonzero and is greater than the first axial distance.

2. The system of claim 1, further comprising a seal positioned between the first plunger and the second plunger.

3. The system of claim 1, wherein the evacuable chamber includes a vent dimensioned to provide a reduced air pressure in the evacuable chamber when the first plunger and the second plunger are moved from the first position to the second position and further dimensioned to allow air ingress at a desired rate to move the first plunger from its second position to its third position.

4. The system of claim 1, wherein at least one of the first plunger and the second plunger is dimensioned to receive at least a portion of the second plunger and the first plunger, respectively.

5. The system of claim 1, wherein the first plunger and the second plunger include inter-engaging structures.

6. The system of claim 1, wherein the first plunger includes an outer sleeve portion dimensioned to receive at least a portion of the second plunger, such that the first plunger forms an outer plunger and the second plunger forms an inner plunger.

7. The system of claim 1, wherein the first plunger includes an annular recess dimensioned to receive an annular projection of the second plunger.

8. The system of claim 7, wherein the annular projection extends axially away from a medicament canister of the medicinal inhaler.

9. The system of claim 1, wherein the second plunger includes a central tubular recess dimensioned to receive a central tubular projection of the first plunger.

10. The system of claim 1, wherein the second plunger includes an annular recess dimensioned to receive at least a portion of an adapter configured to house at least a portion of the medicament canister of the medicinal inhaler.

11. The system of claim 1, wherein the first plunger is configured to be operatively coupled to the medicament canister of the medicinal inhaler via an adapter configured to house at least a portion of the medicament canister.

12. The system of claim 1, wherein the first plunger and the second plunger are rotationally fixed with respect to the axis.

13. The system of claim 1, further comprising:

a guideway, wherein at least a portion of the guideway has a helical shape, the guideway having a first portion having a first helix angle with respect to the axis that is greater than zero, and a second portion having a second helix angle with respect to the axis, wherein the second helix angle is less than the first helix angle; and a projection dimensioned to be received in the guideway, the projection being movable in the guideway between a first position corresponding to the first position of the first plunger and a second position corresponding to the second position of the second plunger, such that the projection is configured to be cammed along the guideway when the stored energy device drives the second plunger to move from the first position to the second position;

wherein the guideway or the projection is fixedly coupled to the second plunger.

14. The system of claim 1, wherein the stored energy device is configured to provide at least 40 N of force when the stored energy is released.

15. The system of claim 1, wherein the firing system is breath-actuated.

16. A medicinal inhaler comprising the auto-reset dose release firing system of claim 1, wherein the medicinal inhaler is a pressurized metered dose inhaler (pMDI).

\* \* \* \* \*